United States Patent
Suri et al.

(10) Patent No.: US 11,642,529 B2
(45) Date of Patent: *May 9, 2023

(54) STIMULATOR SYSTEMS AND METHODS FOR OBSTRUCTIVE SLEEP APNEA

(71) Applicant: THE ALFRED E. MANN FOUNDATION FOR SCIENTIFIC RESEARCH, Valencia, CA (US)

(72) Inventors: Harshit Suri, Pasadena, CA (US); Joseph L. Calderon, Culver City, CA (US); Gregory Frederick Molnar, Blaine, MN (US); George S. Goding, Jr., Minneapolis, MN (US); Alanie Atyabi, Chatsworth, CA (US); Siegmar Schmidt, Simi Valley, CA (US); William Dai, Ventura, CA (US); Brian Dearden, Pasadena, CA (US); Desmond B. Keenan, Valencia, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 207 days.

This patent is subject to a terminal disclaimer.

(21) Appl. No.: 17/091,182

(22) Filed: Nov. 6, 2020

(65) Prior Publication Data
US 2021/0052893 A1 Feb. 25, 2021

Related U.S. Application Data

(63) Continuation of application No. 16/992,439, filed on Aug. 13, 2020, which is a continuation of application
(Continued)

(51) Int. Cl.
*A61N 1/36* (2006.01)
*A61B 1/267* (2006.01)
(Continued)

(52) U.S. Cl.
CPC ............ *A61N 1/3611* (2013.01); *A61B 1/267* (2013.01); *A61B 5/0836* (2013.01);
(Continued)

(58) Field of Classification Search
None
See application file for complete search history.

(56) References Cited

U.S. PATENT DOCUMENTS 3,677,261 A   7/1972 Day
4,602,624 A   7/1986 Naples
(Continued)

FOREIGN PATENT DOCUMENTS

| EP | 2478931 | 12/2015 |
|---|---|---|
| WO | WO2008048471 | 4/2008 |
| WO | WO2009135138 | 11/2009 |

OTHER PUBLICATIONS

PCT International Search Report for PCT/US2018/016287, Applicant: The Alfred E. Mann Foundation for Scientific Research, Form PCT/ISA/210 and 220, dated Jun. 6, 2018 (6 pages).
(Continued)

*Primary Examiner* — Catherine M Voorhees
*Assistant Examiner* — Elizabeth K So
(74) *Attorney, Agent, or Firm* — Michael J. Bolan; Vista IP Law Group, LLP

(57) ABSTRACT

An electrode lead comprises an electrically insulative cuff body and at least three axially aligned electrode contacts circumferentially disposed along the inner surface of the cuff body when in the furled state. The electrode contacts may be circumferentially disposed around a nerve, and an electrical pulse train may be delivered to the electrode contacts thereby stimulating the nerve to treat obstructive sleep apnea. The electrical pulse train may be one that preconditions peripherally located nerve fascicles to not be
(Continued)

stimulated, while stimulating centrally located nerve fascicles. A feedback mechanism can be used to titrate electrode contacts and electrical pulse train to the patient. A sensor that is affixed to the case of a neurostimulator can be used to measure physiological artifacts of respiration, and a motion detector can be used to sense tapping of the neurostimulator to toggle the neurostimulator between an ON position and an OFF position.

27 Claims, 13 Drawing Sheets

Related U.S. Application Data

No. 16/245,509, filed on Jan. 11, 2019, now abandoned, which is a continuation of application No. 15/885,618, filed on Jan. 31, 2018, now abandoned.

(60) Provisional application No. 62/453,311, filed on Feb. 1, 2017.

(51) Int. Cl.
| | | |
|---|---|---|
| A61B 5/083 | (2006.01) | |
| A61B 5/087 | (2006.01) | |
| A61N 1/05 | (2006.01) | |
| A61N 1/378 | (2006.01) | |
| A61B 5/00 | (2006.01) | |
| A61N 1/372 | (2006.01) | |
| A61B 5/394 | (2021.01) | |

(52) U.S. Cl.
CPC ............ *A61B 5/0878* (2013.01); *A61B 5/394* (2021.01); *A61B 5/4818* (2013.01); *A61B 5/4836* (2013.01); *A61N 1/0556* (2013.01); *A61N 1/3601* (2013.01); *A61N 1/36139* (2013.01); *A61N 1/3787* (2013.01); *A61N 1/37211* (2013.01); *A61B 2562/0219* (2013.01)

(56) References Cited

U.S. PATENT DOCUMENTS

| | | | |
|---|---|---|---|
| 4,830,008 A | 5/1989 | Meer | |
| 5,123,425 A | 6/1992 | Shannon | |
| 5,146,918 A | 9/1992 | Kallok | |
| 5,158,080 A | 10/1992 | Kallok | |
| 5,174,287 A | 12/1992 | Kallok | |
| 5,178,156 A | 1/1993 | Takishima | |
| 5,211,173 A | 5/1993 | Kallok | |
| 5,215,082 A | 6/1993 | Kallok | |
| 5,277,193 A | 1/1994 | Takishima | |
| 5,300,094 A | 4/1994 | Kallok | |
| 5,304,206 A * | 4/1994 | Baker, Jr. | A61N 1/37217 607/45 |
| 5,335,657 A | 8/1994 | Terry | |
| 5,483,969 A | 1/1996 | Testerman | |
| 5,522,862 A | 6/1996 | Testerman | |
| 5,540,731 A | 7/1996 | Testerman | |
| 5,540,732 A | 7/1996 | Testerman | |
| 5,540,733 A | 7/1996 | Testerman | |
| 5,546,952 A | 8/1996 | Erickson | |
| 5,549,655 A | 8/1996 | Erickson | |
| 5,591,216 A | 1/1997 | Testerman | |
| 5,944,680 A | 8/1999 | Christopherson | |
| 6,066,165 A | 5/2000 | Racz | |
| 7,660,632 B2 | 2/2010 | Kirby | |
| 7,809,442 B2 | 10/2010 | Bolea | |
| 8,155,757 B1 | 4/2012 | Neisz | |
| 8,340,785 B2 | 12/2012 | Bonde | |
| 8,428,727 B2 | 4/2013 | Bolea | |
| 8,718,776 B2 | 5/2014 | Mashiach | |
| 8,718,783 B2 | 5/2014 | Bolea | |
| 8,934,992 B2 | 1/2015 | Johnson | |
| 8,938,299 B2 | 1/2015 | Christopherson | |
| 8,983,572 B2 | 3/2015 | Ni | |
| 9,186,511 B2 | 11/2015 | Bolea | |
| 9,314,641 B2 | 4/2016 | Meadows | |
| 9,452,293 B2 | 9/2016 | Rondoni | |
| 9,486,628 B2 | 11/2016 | Christopherson | |
| 9,555,247 B2 | 1/2017 | Tesfayesus | |
| 2010/0094379 A1 | 4/2010 | Meadows et al. | |
| 2010/0174341 A1 | 7/2010 | Bolea | |
| 2011/0112601 A1 | 5/2011 | Meadows et al. | |
| 2011/0202119 A1 | 8/2011 | Ni | |
| 2012/0192874 A1 | 8/2012 | Bolea | |
| 2013/0204097 A1 | 8/2013 | Rondoni | |
| 2013/0338749 A1 | 12/2013 | Brunnett | |
| 2014/0228905 A1* | 8/2014 | Bolea | A61N 1/3611 607/42 |
| 2015/0174396 A1 | 6/2015 | Fisher | |
| 2015/0224307 A1 | 8/2015 | Bolea | |
| 2016/0059011 A1 | 3/2016 | Bolea | |
| 2016/0263376 A1* | 9/2016 | Yoo | A61N 1/36017 |
| 2016/0303388 A1 | 10/2016 | Rondoni | |

OTHER PUBLICATIONS

PCT Written Opinion of the International Search Authority for PCT/US2018/016287,, Applicant: The Alfred E. Mann Foundation for Scientific Research, Form PCT/ISA/237, dated Jun. 6, 2018 (6 pages).

International Preliminary Report on Patentability for PCT/US2018/016287, Applicant: The Alfred E. Mann Foundation for Scientific Research, Form PCT/IB/373 and 237, dated Aug. 6, 2019 (8 pages).

\* cited by examiner

STIMULATOR SYSTEMS AND METHODS FOR OBSTRUCTIVE SLEEP APNEA

RELATED APPLICATION DATA

This application is a continuation of U.S. patent application Ser. No. 16/992,439, filed Aug. 13, 2020, which is a continuation of U.S. patent application Ser. No. 16/245,509, filed Jan. 11, 2019 (now abandoned), which is a continuation of U.S. patent application Ser. No. 15/885,618, filed Jan. 31, 2018 (now abandoned), which claims the benefit of U.S. Provisional Patent Application Ser. No. 62/453,311, filed Feb. 1, 2017. The contents of the aforementioned patent applications are hereby expressly incorporated by reference in their entirety.

FIELD OF THE INVENTION

The present invention relates to systems and methods for the treatment of obstructive sleep apnea (OSA).

BACKGROUND

OSA is a highly prevalent sleep disorder that is caused by the collapse of or increase in the resistance of the pharyngeal airway, often resulting from tongue obstruction. The obstruction of the upper airway is mainly caused by reduced genioglossus muscle activity during the deeper states of NREM sleep. Obstruction of the upper airway causes breathing to pause during sleep. Cessation of breathing causes a decrease in the blood oxygen saturation level, which is eventually corrected when the person wakes up and resumes breathing. The long-term effects of OSA include high blood pressure, heart failure, strokes, diabetes, headaches, and general daytime sleepiness and memory loss, among other symptoms.

OSA is extremely common, having a similar prevalence as diabetes or asthma. Over 100 million people worldwide suffer from OSA, with about 25% of those being treated. Continuous Positive Airway Pressure (CPAP) is the usual established therapy for people who suffer from OSA. More than five million patients own a CPAP machine in North America, but many do not comply with use of these machines, because they cover the mouth and nose and, hence, are cumbersome and uncomfortable.

The use of neurostimulators to open the upper airway has been explored by several companies as a treatment for alleviating apneic events. Such therapy involves stimulating the nerve fascicles of the hypoglossal nerve (HGN) that innervate the intrinsic and extrinsic muscles of the tongue in a manner that prevents retraction of the tongue, which would otherwise close the upper airway during inspiration of the respiratory cycle.

ImThera Medical is currently in FDA clinical trials for a stimulator system that is used to stimulate the trunk of the HGN with a nerve cuff electrode. The stimulation system does not provide a sensor or sensing, and therefore, the stimulation delivered to the HGN trunk is not synchronized to the respiratory cycle. Thus, the tongue and other muscles that are innervated by nerve fascicles of the HGN trunk are stimulated irrespective of the respiratory cycle.

The rationale for this treatment method appears to be that it is enough simply to tone the tongue muscle and other nearby muscles, so that the tongue muscle does not retract in a manner that would cause OSA. The belief is that it is not necessary to specifically target the protraction (i.e., anterior movement) of the tongue muscle and to synchronize the occurrence of tongue protraction when it is most needed, i.e., during inspiration. The nerve cuff electrode of the ImThera Medical system has multiple electrode contacts helically surrounding the proximal part of the HGN nerve trunk. So, instead, each electrode contact delivers stimulation in a sequential order to the HGN trunk. For example, if a three-electrode contact nerve cuff is used, electrode contact #1 stimulates, then stops, electrode contact #2 stimulates, then stops, electrode contact #3 stimulates, then stops, then electrode contact #1 stimulates, then stops and so on. Since all or most electrode contacts deliver stimulation, there is no selection process to choose the best one or two electrode contacts that is finally used to deliver the best stimulation to alleviate sleep apnea.

A disadvantage of the ImThera Medical system is that it does not target tongue protraction coincident with the inspiration phase of respiration, since it does not have a sensor to enable synchronization of stimulation to the respiratory cycle. Since there is no attempt to synchronize the stimulation with the respiratory cycle, the tongue protraction does not occur when it would appear to help the most—during inspiration when OSA can occur. Also, because the HGN trunk contains nerve fascicles that innervate muscles other than the muscle that extend the tongue, the Imthera Medical method of stimulation at the HGN trunk does not just target the specific protrusor muscles of the tongue muscle, but other muscles that are not targeted. Thus, stimulating the HGN trunk in an arbitrary manner may recruit other nerve fascicles of the HGN trunk that may not contribute to the protraction of the tongue.

Another company, Inspire Medical Systems, Inc., does offer a stimulation system with a sensor, and therefore does attempt to time the onset of stimulation to the breathing cycle. This system, which is FDA approved for sale in the United States since April 2010, uses a simple, bipolar electrode (two electrode contacts only) within a nerve cuff electrode and implants the electrode at the branch of the HGN that is responsible for protruding the tongue. A simple, two-electrode contact or three-electrode contact cuff electrode can be used at the branch nerve, unlike the HGN trunk, because at the distal branch location, the nerve fascicles generally innervate the specific tongue protrusor muscle and not other muscles.

However, implanting the electrode at a branch of the HGN takes additional surgery time, which increases trauma to the patient and increases the substantial expense of operating room time. By attaching the nerve cuff electrode to the proximal section of the main trunk of the HGN, compared to placing the nerve cuff electrode at the more distal end of the HGN, it estimated that the surgical time will be reduced by approximately one hour. Even more importantly, because the branch nerve is small and more difficult to isolate than the HGN trunk, implanting a nerve cuff electrode at the branch site demands heightened expertise from the otolaryngologist/Ear Nose and Throat (ENT) surgeon or neurosurgeon, which significantly increases the chance for error and surgical risks. Furthermore, because the distal location of the HGN has a smaller diameter of nerves, and hence the required electrodes need to be smaller, the smaller nerve cuff electrode may be more difficult to manufacture.

Thus, it is certainly desirable to implant the nerve cuff electrode at the trunk of the hypoglossal nerve. However, one must then deal with the fact that the target nerve fascicles may be near the center of the nerve trunk and are not easily isolated and stimulated, while at the same time avoiding stimulating other non-targeted fascicles in the same nerve trunk.

Furthermore, a pressure sensor is connected to neurostimulator of the Inspire system by a lead, thereby allowing the pressure sensor to be placed remotely from the implanted site of the neurostimulator. However, the fact that the pressure sensor has a lead connected to the stimulator necessitates some additional surgery, because the sensor lead is another appendage that must be implanted.

There, thus, remains a need for improved systems and methods for selectively recruiting only the fascicles of the hypoglossal nerve in synchronization with the respiratory cycle for treating OSA of a patient, while minimizing the surgery time and effort required to implant the neurostimulation components in the patient.

SUMMARY

In accordance with a first aspect of the present inventions, an electrode lead comprises an elongated lead body having a proximal end and a distal end, and at least three connector contacts affixed to the proximal end of the lead body. In one embodiment, the lead body has at least one portion that is S-shaped to provide strain relief. The electrode lead further comprises a biologically compatible, flexible, electrically insulative cuff body affixed to the distal end of the lead body. The cuff body is pre-shaped to transition from an unfurled state to a furled state, wherein the cuff body, when in the furled state has an inner surface for contacting a nerve. In one embodiment, the inner surface of the furled cuff body has a diameter in the range of 2.5 mm to 4.0 mm. In another embodiment, the cuff body is self-adjusting, such that the cuff body accommodates different sized nerve diameters, and diameter changes over time.

The electrode lead further comprises at least three axially aligned electrode contacts circumferentially disposed along the inner surface of the cuff body when in the furled state, and at least three electrical conductors extending through the lead body respectively between the at least three connector contacts and the electrode contacts. In one embodiment, when the cuff body is in the furled state, the electrode contacts circumferentially span at least a 180-degree arc around the inner surface of the cuff body. In another embodiment, when the cuff body is in the furled state, the electrode contacts circumferentially span at least a 270-degree arc around the inner surface of the cuff body. In still another embodiment, when the cuff body is in the unfurled state, a center-to-center spacing of each pair of adjacent ones of electrode contacts is equal to or less than twice the width of each electrode contact of the respective pair of electrode contacts.

A neurostimulation system may comprise the electrode lead described above, and a neurostimulator comprising a connector configured for receiving the proximal contacts of the electrode lead, stimulation circuitry configured for generating an electrical pulse train, and control circuitry configured for causing the stimulation circuitry to deliver the electrical pulse train to at least one of the electrode contacts of the electrode lead. A method of using the electrode lead described above may comprise maintaining the cuff body in the unfurled state while placing the cuff body in contact with the nerve, placing the cuff body from the unfurled state into the furled state, such that the cuff body wraps around the nerve, and delivering an electrical pulse train to at least one of the electrode contacts of the electrode lead, thereby stimulating the nerve.

In accordance with a second aspect of the present inventions, a neurostimulation system comprises an electrode lead having a lead body. In one embodiment, the lead body has at least one portion that is S-shaped to provide strain relief. The electrode lead further comprises a biologically compatible electrically insulative cuff body affixed to the distal end of the lead body. The cuff body is pre-shaped and flexible to transition from an unfurled state to a furled state. The cuff body, when in the furled state has an inner surface for contacting a nerve. In one embodiment, the inner surface of the furled cuff body has a diameter in the range of 2.5 mm to 4.0 mm. In another embodiment, the cuff body is self-adjusting, such that the cuff body accommodates different sized nerve diameters, and diameter changes over time.

The electrode lead further comprises at least three axially aligned electrode contacts circumferentially disposed along the inner surface of the cuff body when in the furled state. In one embodiment, when the cuff body is in the furled state, the electrode contacts circumferentially span at least a 180-degree arc around the inner surface of the cuff body. In another embodiment, when the cuff body is in the furled state, the electrode contacts circumferentially span at least a 270-degree arc around the inner surface of the cuff body. In still another embodiment, when the cuff body is in the unfurled state, a center-to-center spacing of each pair of adjacent ones of electrode contacts is equal to or less than twice the width of each electrode contact of the respective pair of electrode contacts.

The neurostimulation system further comprises a neurostimulator configured for delivering an electrical pulse train to at least one of the electrode contacts of the electrode lead. By way of example, the electrical pulse train may have an initial, preconditioning current or voltage amplitude and a subsequent higher stimulating current or voltage amplitude. In one embodiment, the electrode contacts comprise a pair of adjacent ones of the electrode contacts, and the neurostimulator is configured for delivering the electrical pulse train between the pair of adjacent ones of the electrode contacts in a bipolar mode. In another embodiment, the neurostimulator is further configured for sensing physiological artifacts that are caused by respiration, and delivering the electrical pulse train to the electrode contacts in synchronization with a respiratory cycle based on the sensed physiological artifacts. As one example, the neurostimulator may be configured for determining the next projected onset of an inspiratory phase of the respiratory cycle based on the sensed physiological artifacts, and delivering the electrical pulse train to the at least one electrode contact immediately before, at, or right after the next projected onset of the inspiratory phase of the respiratory cycle. In another embodiment, the neurostimulator is configured for storing data representative of the physiological artifacts sensed by the sensing circuitry.

The neurostimulation system may optionally comprise a clinician programmer configured for selecting the electrode contacts, and transcutaneously communicating with the neurostimulator, and programming the neurostimulator to deliver the electrical pulse train to the selected electrode contact; a patient programmer configured for transcutaneously communicating with the neurostimulator, and toggling the neurostimulator between an OFF position and an ON position, such that in the OFF position, no stimulation is delivered; and/or an external charger configured for inductively and transcutaneously charging the neurostimulator.

The neurostimulation system may optionally comprise a feedback mechanism configured for measuring a physiological parameter of the patient indicative of the efficacy of the delivered electrical pulse train in treating obstructive sleep apnea of a patient. As examples, the feedback mechanism may comprise one or more temperature sensors configured for measuring the temperature of inhaled and exhaled air of a patient, one or more carbon dioxide ($CO_2$) sensors configured for measuring a concentration of $CO_2$ in inhaled and exhaled air of the patient, one or more electro-myographic (EMG) sensors configured for measuring the electrical potential generated by the muscle cells of a tongue of the patient, one or more cameras configured for capturing pictures of the airway of the patient, or one or more inertial sensors configured for measuring the movement of the tongue of the patient. If the neurostimulation system comprises a clinician programmer, it can be configured for computing a score of the at least one electrode based on the measured physiological parameter.

In accordance with a third aspect of the present inventions, a method of stimulating a nerve (e.g., a trunk of a hypoglossal nerve (HGN)) of a patient to treat an ailment (e.g., obstructive sleep apnea (OSA)) comprises circumferentially disposing at least three axially aligned electrode contacts around the nerve (e.g., on the HGN trunk proximal to a medical branch of the HGN trunk). In one method, the nerve has a diameter in the range of 2.5 mm to 4.0 mm. In another method, the electrode contacts circumferentially span at least a 180-degree arc around nerve. In still another method, the electrode contacts circumferentially span at least a 270-degree arc around the nerve. In yet another method, a center-to-center spacing of each pair of adjacent ones of electrode contacts is equal to or less than twice the width of each electrode contact of the respective pair of electrode contacts.

The method further comprises delivering an electrical pulse train to at least one of the electrode contacts, thereby stimulating the nerve to treat the ailment. The electrode contacts may comprise a pair of adjacent ones of the electrode contacts, and the electrical pulse train is delivered between the pair of adjacent ones of the electrode contacts in a bipolar mode. In one exemplary method, the electrical pulse train has an initial, preconditioning current or voltage amplitude and a subsequent higher stimulating current or voltage amplitude, such that one or more peripherally located nerve fascicles in the nerve are pre-conditioned by the initial preconditioning current or voltage amplitude, and one or more centrally located nerve fascicles in the nerve further away from the at least one electrode than the peripherally located nerve fascicles are triggered by the higher stimulating current or voltage amplitude, while the one or more pre-conditioned peripherally located nerve fascicles are not triggered by the higher stimulating current or voltage amplitude.

An optional method further comprises sensing physiological artifacts that are caused by respiration, and delivering the electrical pulse train to the electrode contacts in synchronization with a respiratory cycle based on the sensed physiological artifacts. As one example, the method may further comprise determining the next projected onset of an inspiratory phase of the respiratory cycle based on the sensed physiological artifacts, and delivering the electrical pulse train to the electrode contacts immediately before, at, or right after the next projected onset of the inspiratory phase of the respiratory cycle. The method may further comprise storing data representative of the sensed physiological artifacts.

Another optional method further comprises measuring a physiological parameter of the patient indicative of the efficacy of the delivered electrical pulse train in treating an ailment of a patient. As examples, the physiological parameter may comprise one or more of measuring the temperature of inhaled and exhaled air of a patient, measuring a concentration of $CO_2$ in inhaled and exhaled air of the patient, measuring the electrical potential generated by the muscle cells of a tongue of the patient, capturing pictures of the airway of the patient, and measuring the movement of the tongue of the patient. The method may further comprise computing a score of the at least one electrode based on the measured physiological parameter.

In accordance with a fourth aspect of the present inventions, another method of stimulating a nerve (e.g., a trunk of a hypoglossal nerve (HGN)) of a patient to treat an ailment (e.g., obstructive sleep apnea (OSA)) comprises disposing at least one electrode contact adjacent the nerve (e.g., on the HGN trunk proximal to a medical branch of the HGN trunk), and delivering an electrical pulse train to the electrode contact(s), thereby treating the ailment. The nerve has one or more peripherally located nerve fascicles and one or more centrally located nerve fascicles further away from the electrode contact(s) than the peripherally located nerve fascicles, and electrical pulse train has an initial, preconditioning current or voltage amplitude and a subsequent higher stimulating current or voltage amplitude, such that the one or more peripherally located nerve fascicles are pre-conditioned by the initial preconditioning current or voltage amplitude, and the centrally located nerve fascicle(s) are triggered by the higher stimulating current or voltage amplitude, while the one or more pre-conditioned peripherally located nerve fascicles are not triggered by the higher stimulating current or voltage amplitude.

In one method, the nerve has a diameter in the range of 2.5 mm to 4.0 mm. In another method, the electrode contact(s) comprises a plurality of electrode contacts circumferentially disposed around the nerve. The electrode contacts may, e.g., be axially aligned with each other, and may circumferentially span at least a 180-degree arc around the nerve, or even at least a 270-degree arc around the nerve. In still another method, a center-to-center spacing of each pair of adjacent ones of electrode contacts is equal to or less than twice the width of each electrode contact of the respective pair of electrode contacts. In still another method, the electrode contact(s) comprises a pair of adjacent ones of the electrode contacts, and the electrical pulse train is delivered between the pair of adjacent ones of the electrode contacts in a bipolar mode.

An optional method further comprises sensing physiological artifacts that are caused by respiration, and delivering the electrical pulse train to the electrode contact(s) in synchronization with a respiratory cycle based on the sensed physiological artifacts. As one example, the method may further comprise determining the next projected onset of an inspiratory phase of the respiratory cycle based on the sensed physiological artifacts, and delivering the electrical pulse train to the electrode contact(s) immediately before, at, or right after the next projected onset of the inspiratory phase of the respiratory cycle. The method may further comprise storing data representative of the sensed physiological artifacts.

Another optional method further comprises measuring a physiological parameter of the patient indicative of the efficacy of the delivered electrical pulse train in treating an ailment of a patient. As examples, the physiological parameter may comprise one or more of measuring the temperature of inhaled and exhaled air of a patient, measuring a concentration of $CO_2$ in inhaled and exhaled air of the patient, measuring the electrical potential generated by the muscle cells of a tongue of the patient, capturing pictures of the airway of the patient, and measuring the movement of the tongue of the patient. The method may further comprise computing a score of the at least one electrode based on the measured physiological parameter.

In accordance with a fifth aspect of the present inventions, a neurostimulation system for treating obstructive sleep apnea (OSA) in a patient comprises an electrode lead carrying at least one of the electrode contacts. In one embodiment, the electrode lead comprises a lead body, and a biologically compatible, flexible, electrically insulative cuff body affixed to distal end of the lead body. In this case, the cuff body may be pre-shaped to transition from an unfurled state to a furled state, the cuff body, when in the furled state has an inner surface for contacting a nerve, and the at least one electrode contact(s) comprises a plurality of electrode contacts circumferentially disposed along the inner surface of the cuff body when in the furled state. The inner surface of the furled cuff body has a diameter in the range of 2.5 mm to 4.0 mm, the cuff body may be self-adjusting, such that the cuff body accommodates different sized nerve diameters, and diameter changes over time, and the electrode contacts may be axially aligned with each other.

In one embodiment, when the cuff body is in the furled state, the electrode contacts circumferentially span at least a 180-degree arc around the inner surface of the cuff body. In another embodiment, when the cuff body is in the furled state, the electrode contacts circumferentially span at least a 270-degree arc around the inner surface of the cuff body. In still another embodiment, when the cuff body is in the unfurled state, a center-to-center spacing of each pair of adjacent ones of electrode contacts is equal to or less than twice the width of each electrode contact of the respective pair of electrode contacts.

The neurostimulation system further comprises a neurostimulator configured for delivering an electrical pulse train to the electrode contact(s). By way of example, the electrical pulse train may have an initial, preconditioning current or voltage amplitude and a subsequent higher stimulating current or voltage amplitude. In one embodiment, the electrode contact(s) comprises a pair of adjacent ones of the electrode contacts, and the neurostimulator is configured for delivering the electrical pulse train between the pair of adjacent ones of the electrode contacts in a bipolar mode. In another embodiment, the neurostimulator is further configured for sensing physiological artifacts that are caused by respiration, and delivering the electrical pulse train to the electrode contacts in synchronization with a respiratory cycle based on the sensed physiological artifacts. As one example, the neurostimulator may be configured for determining the next projected onset of an inspiratory phase of the respiratory cycle based on the sensed physiological artifacts, and delivering the electrical pulse train to the at least one electrode contact immediately before, at, or right after the next projected onset of the inspiratory phase of the respiratory cycle. In another embodiment, the neurostimulator is configured for storing data representative of the physiological artifacts sensed by the sensing circuitry.

The neurostimulation system may optionally comprise a clinician programmer configured for selecting the electrode contacts, and transcutaneously communicating with the neurostimulator, and programming the neurostimulator to deliver the electrical pulse train to the selected electrode contact; a patient programmer configured for transcutaneously communicating with the neurostimulator, and toggling the neurostimulator between an OFF position and an ON position, such that in the OFF position, no stimulation is delivered; and/or an external charger configured for inductively and transcutaneously charging the neurostimulator.

The neurostimulation system further comprises a feedback mechanism configured for measuring a physiological parameter of the patient indicative of an efficacy of the delivered electrical pulse train in treating the OSA. As examples, the feedback mechanism may comprise one or more temperature sensors configured for measuring the temperature of inhaled and exhaled air of a patient, one or more carbon dioxide ($CO_2$) sensors configured for measuring a concentration of $CO_2$ in inhaled and exhaled air of the patient, one or more electro-myographic (EMG) sensors configured for measuring the electrical potential generated by the muscle cells of a tongue of the patient, one or more cameras configured for capturing pictures of the airway of the patient, and one or more inertial sensors configured for measuring the movement of the tongue of the patient.

If the neurostimulation system comprises a clinician programmer, it can be configured for computing a score of the at least one electrode based on the measured physiological parameter. For example, the clinician programmer may be configured for determining the efficiency of each inspiration phase in the respiratory cycle based on the measured physiological parameter, and computing the score based on the determined efficiency of each inspiration phase in the respiratory cycle.

In one embodiment, the feedback mechanism comprises one or more temperature sensors, the measured physiological parameter is a peak-to-peak difference in temperature of inhaled and exhaled air of the patient, the clinician programmer determines the efficiency of each inspiration phase in the respiratory cycle based on the measured physiological parameter, and computes the score based on the determined efficiency of each inspiration phase in the respiratory cycle.

In another embodiment, the feedback mechanism comprises one or more carbon dioxide ($CO_2$) sensors, the measured physiological parameter is a peak-to-peak difference in the concentration of $CO_2$ in inhaled and exhaled air of the patient, the clinician programmer determines the efficiency of each inspiration phase in the respiratory cycle based on the measured physiological parameter, and computes the score based on the determined efficiency of each inspiration phase in the respiratory cycle.

In still another embodiment, the feedback mechanism comprises one or more electro-myographic (EMG) sensors, the measured physiological parameter is an electrical potential generated by the muscle cells of a tongue of the patient, and the clinician programmer determines the extent to which one or more tongue protusor muscles are activated based on the measured physiological parameter, and computes the score based on the determined extent to which the one or more tongue protrusor muscles are activated.

In yet another embodiment, the feedback mechanism comprises one or more cameras, the physiological parameter is a picture of the airway of the patient, clinician programmer determines the extent to which the airway of the patient is obstructed based on the measured physiological parameter, and computes the score based on the determined extent to which the airway of the patient is obstructed.

In still yet another embodiment, the feedback mechanism comprises one or more inertial sensors, the measured physiological parameter comprises is the movement of the tongue of the patient, the clinician programmer determines the extent to which the tongue of the patient protrudes based on the measured physiological parameter, and computes the score based on the determined extent to which the tongue of the patient protrudes.

In accordance with a sixth aspect of the present inventions, a method of titrating (or equivalently, "fitting") a neurostimulation system that treats obstructive sleep apnea (OSA) comprises circumferentially disposing a plurality of electrode contacts around a trunk of a hypoglossal nerve (HGN) (e.g., on the HGN trunk proximal to a medial branch of the HGN trunk). In one method, the nerve has a diameter in the range of 2.5 mm to 4.0 mm. In another method, the electrode contacts circumferentially span at least a 180-degree arc around nerve. In still another method, the electrode contacts circumferentially span at least a 270-degree arc around the nerve. In yet another method, a center-to-center spacing of each pair of adjacent ones of electrode contacts is equal to or less than twice the width of each electrode contact of the respective pair of electrode contacts.

The method further comprises sequentially delivering an electrical pulse train to each of a plurality of sets of the electrode contacts. As one example, each set of electrode contacts may comprise a pair of adjacent ones of the electrode contacts, in which case, the electrical pulse train may be sequentially delivered to each set of electrode contacts in a bipolar mode. As another example, each set of electrode contacts may comprise a single electrode contact and the neurostimulator (or IPG) housing the indifferent or return electrode, in which case, the electrical pulse may be sequentially delivered to each electrode contact or set of contacts in a monopolar mode. And in some cases, non-adjacent electrode contact pairs or even more than two non-adjacent contacts may be chosen for either bipolar or monopolar stimulation.

In one exemplary method, the electrical pulse train has an initial, preconditioning current or voltage amplitude and a subsequent higher stimulating current or voltage amplitude, such that one or more peripherally located nerve fascicles in the nerve are pre-conditioned by the initial preconditioning current or voltage amplitude, and one or more centrally located nerve fascicles in the nerve further away from the at least one electrode than the peripherally located nerve fascicles are triggered by the higher stimulating current or voltage amplitude, while the one or more pre-conditioned peripherally located nerve fascicles are not triggered by the higher stimulating current or voltage amplitude.

The method further comprises measuring a physiological parameter of the patient indicative of an efficacy of the delivered electrical pulse train in treating the OSA. As examples, the physiological parameter may comprise one or more of measuring the temperature of inhaled and exhaled air of a patient, measuring a concentration of $CO_2$ in inhaled and exhaled air of the patient, measuring the electrical potential generated by the muscle cells of a tongue of the patient, capturing pictures of the airway of the patient, and measuring the movement of the tongue of the patient.

The method further comprises selecting one of the sets of electrode contacts based on the measured physiological parameter. In one method, the electrical pulse train is delivered from a neurostimulator, in which case, the method may further comprise programming the neurostimulator with the selected set of electrode contacts. The method may further comprise computing a score of each of the electrode contact sets based on the respective measured physiological parameter. One method further comprises determining the efficiency of each inspiration phase in the respiratory cycle based on the measured physiological parameter, and computing the score based on the determined efficiency of each inspiration phase in the respiratory cycle The measured physiological parameter may comprise a peak-to-peak difference in temperature of inhaled and exhaled air of the patient, and the method may further comprise determining the efficiency of each inspiration phase in the respiratory cycle based on the measured peak-to-peak difference in temperature of inhaled and exhaled air of the patient, in which case, the score may be computed based on the determined efficiency of each inspiration phase in the respiratory cycle.

The measured physiological parameter may comprise a peak-to-peak difference in the concentration of $CO_2$ in inhaled and exhaled air of the patient, and the method further comprises determining the efficiency of each inspiration phase in the respiratory cycle based on the measured peak-to-peak difference in the concentration of $CO_2$ in inhaled and exhaled air of the patient, in which case, the score may be computed based on the determined efficiency of each inspiration phase in the respiratory cycle.

The measured physiological parameter may comprise an electrical potential generated by the muscle cells of a tongue of the patient, the method further comprising determining the extent to which one or more tongue protusor muscles are activated based on the measured electrical potential generated by the muscle cells of a tongue of the patient, in which case, the score may be computed based on the determined extent to which the one or more tongue protrusor muscles are activated.

The measured physiological parameter may comprise a picture of the airway of the patient, and the method may further comprises determining the extent to which the airway of the patient is obstructed based on the picture of the airway of the patient, in which case, the score may be computed based on the determined extent to which the airway of the patient is obstructed.

The measured physiological parameter may comprise a movement of the tongue of the patient, and the method may further comprise determining the extent to which the tongue of the patient protrudes based on the movement of the tongue of the patient, in which case, the score may be computed based on the determined extent to which the tongue of the patient protrudes.

In accordance with a seventh aspect of the present inventions, an implantable neurostimulator for use in a patient having obstructive sleep apnea comprises a case and stimulation circuitry contained within the case. The stimulation circuitry is configured for generating an electrical pulse train. In one embodiment, the electrical pulse train has an initial, preconditioning current or voltage amplitude and a subsequent higher stimulating current or voltage amplitude. The neurostimulator further comprises sensing circuitry comprising a sensor (e.g., at least one of a pressure sensor and an inertial sensor) affixed directly to or within the case. The sensor is configured for sensing physiological artifacts that are caused by respiration.

The neurostimulator further comprises control circuitry contained within the case. The control circuitry configured for causing the stimulation circuitry to deliver the electrical pulse train to at least one electrode contact in synchronization with a respiratory cycle based on the sensed physiological artifacts. In one embodiment, the control circuitry is configured for determining the next projected onset of an inspiratory phase of the respiratory cycle based on the sensed physiological artifacts, and causing the stimulation circuitry to deliver the electrical pulse train to the electrode contact(s) immediately before, at, or right after the next projected onset of the inspiratory phase of the respiratory cycle.

In one embodiment, the neurostimulator further comprises a receptacle configured for receiving at least one proximal contact of an electrode lead that carries the electrode contact(s). In another embodiment, the neurostimulator further comprises memory configured for storing data representative of the physiological artifacts sensed by the e sensor(s). The neurostimulator may optionally comprise a motion detector affixed directly to or within the case. The sensor(s) may comprise the motion detector. The motion detector may be configured for sensing a tap on the neurostimulator, and the control circuitry may be configured for toggling the neurostimulator between an ON position and an OFF position in response at least one tap, such that in the OFF position, no stimulation energy is delivered to the at least one electrode contact. As one example, the control circuitry may be configured for toggling the neurostimulator between an ON position and an OFF position in response to a plurality of successive taps (e.g., less than one second apart).

A neurostimulation system may comprise an electrode lead carrying the electrode contact(s), and the neurostimulator, with the receptacle being configured for receiving the electrode lead. The electrode lead may carry a plurality of electrode contacts, in which case, the neurostimulation system may further comprise a clinician programmer configured for selecting the electrode contact(s) from the electrode contacts, transcutaneously communicating with the neurostimulator, and programming the control circuitry to deliver the electrical pulse train to the selected electrode contact(s). The neurostimulation system may further comprise a patient programmer configured for transcutaneously communicating with the neurostimulator, and toggling the neurostimulator between the OFF position and the ON position. The neurostimulator may further comprise a rechargeable battery contained within the case, in which case, the neurostimulation system may further comprise an external charger configured for inductively and transcutaneously charging the rechargeable battery of the neurostimulator.

In accordance with an eighth aspect of the present inventions, an implantable neurostimulator for use in a patient having an ailment comprises a case and stimulation circuitry contained within the case. The stimulation circuitry is configured for generating an electrical pulse train. In one embodiment, the electrical pulse train has an initial, preconditioning current or voltage amplitude and a subsequent higher stimulating current or voltage amplitude.

The neurostimulator further comprises control circuitry contained within the case. The control circuitry is configured for causing the stimulation circuitry to deliver the electrical pulse train to at least one electrode contact. The neurostimulator may further comprise a receptacle configured for receiving at least one proximal contact of an electrode lead that carries the electrode contact(s).

The neurostimulator further comprises a motion detector (e.g., one of a pressure sensor and an inertial sensor) affixed directly to or within the case, the motion detector configured for sensing a tap on the neurostimulator, wherein the control circuitry is configured for toggling the neurostimulator between an ON position and an OFF position in response to a plurality of successive taps, such that in the OFF position, no stimulation energy is delivered to the at least one electrode contact. In one embodiment, the control circuitry is configured for toggling the neurostimulator between an ON position and an OFF position in response to a plurality of successive taps less than one second apart.

In another embodiment, the neurostimulator further comprises sensing circuitry comprising at least one sensor affixed directly to or within the case. The sensor(s) may comprise the motion detector. The sensor(s) is configured for sensing physiological artifacts that are caused by respiration, and the control circuitry is configured for causing the stimulation circuitry to deliver the electrical pulse train in synchronization with a respiratory cycle based on the sensed physiological artifacts. In this case, the control circuitry may be configured for determining the next projected onset of an inspiratory phase of the respiratory cycle based on the sensed physiological artifacts, and causing the stimulation circuitry to deliver the electrical pulse train to the electrode contact(s) immediately before, at, or right after the next projected onset of the inspiratory phase of the respiratory cycle. The neurostimulator may further comprise memory configured for storing data representative of the physiological artifacts sensed by the sensor(s).

A neurostimulation system may comprise an electrode lead carrying the electrode contact(s), and the neurostimulator, with the receptacle being configured for receiving the electrode lead. The electrode lead may carry a plurality of electrode contacts, in which case, the neurostimulation system may further comprise a clinician programmer configured for selecting the electrode contact(s) from the electrode contacts, transcutaneously communicating with the neurostimulator, and programming the control circuitry to deliver the electrical pulse train to the selected electrode contact(s). The neurostimulation system may further comprise a patient programmer configured for transcutaneously communicating with the neurostimulator, and toggling the neurostimulator between the OFF position and the ON position. The neurostimulator may further comprises a rechargeable battery contained within the case, in which case, the neurostimulation system may further comprise an external charger configured for inductively and transcutaneously charging the rechargeable battery of the neurostimulator.

In accordance with a ninth aspect of the present inventions, an implantable neurostimulator is provided for use in a patient having an ailment comprises a case and stimulation circuitry contained within the case. The stimulation circuitry is configured for generating an electrical pulse train. In one embodiment, the electrical pulse train has an initial, preconditioning current or voltage amplitude and a subsequent higher stimulating current or voltage amplitude.

The neurostimulator further comprises sensing circuitry comprising at least one sensor (e.g., one of a pressure sensor and an inertial sensor) affixed directly to or within the case. The sensor(s) is configured for sensing a physiological parameter of patient and sensing a tap on the neurostimulator.

The neurostimulator further comprise control circuitry contained within the case. The control circuitry is configured for causing the stimulation circuitry to deliver the electrical pulse train to at least one electrode contact based on the sensed physiological parameter, and for toggling the neurostimulator between an ON position and an OFF position in response at least one tap, such that in the OFF position, no stimulation energy is delivered to the electrode contact(s). As one example, the control circuitry may be configured for toggling the neurostimulator between an ON position and an OFF position in response to a plurality of successive taps (e.g., less than one second apart). In one embodiment, the neurostimulator further comprises a receptacle configured for receiving at least one proximal contact of an electrode lead that carries the electrode contact(s).

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION

Figure 1:
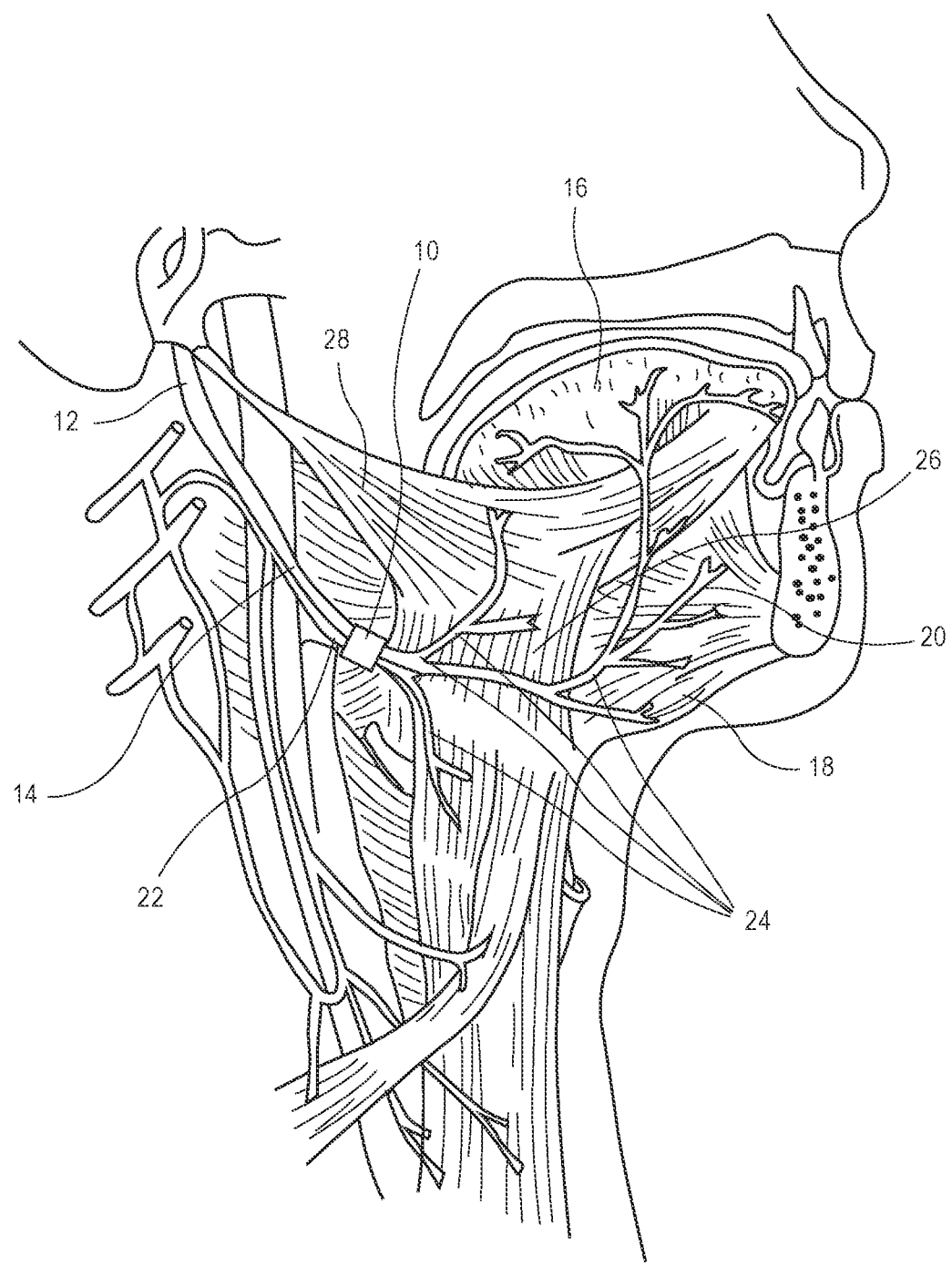
FIG. 1 is a cut-away anatomical drawing of the head and neck area illustrating the muscles that control movement of the tongue and the hypoglossal nerve and its branches that innervate these muscles.

Referring first to FIG. 1, it is desirable to locate a nerve cuff electrode 10 around a trunk 14 of a hypoglossal nerve (HGN) 12 for purposes of stimulating the muscles that move the tongue 16 forward, and in particular, the fascicles of the HGN 12 that innervate the tongue protrusor muscles, such as the genioglossus 18 and/or the geniohyoid muscles 20, thereby preventing or alleviating obstructive apneic events. As shown, the nerve cuff electrode 10 is positioned on the HGN trunk 14 immediately before it branches out, and hence at a proximal position 22 to the HGN branches 24. In the illustrated embodiment, the proximal position 22 is just prior to the medial branch of the HGN 12 that innervates the tongue protrusor muscles.

As briefly discussed above, the implantation of the nerve cuff electrode 10 at this proximal position 22 reduces the surgical time and effort, allows more surgeons to perform the surgery, reduces the risk and trauma to the patient, and reduces engineering design complexity and cost. However, it introduces the problem of inadvertently stimulating other fascicles of the HGN trunk 14 that innervate muscles in opposition to the tongue protrusor muscles, i.e., the tongue retractor muscles, e.g., the hyoglossus 26 and styloglossus muscles 28, as well as the intrinsic muscles of the tongue 16.

As also briefly discussed above, it is further desirable to synchronize the stimulation of the HGN 12 with the respiratory cycle of the patient, so that tongue 16 is anteriorly moved in response to the stimulation of the HGN 12 when it is most needed, and in particular, right before the onset of the next inspiratory phase of the respiratory cycle. Such synchronization requires detection or prediction of the onset of the inspiratory phase using one or more sensors. The conventional thought is that the sensor(s) should be implanted within anatomical structures, such as the ribcage and abdomen, the movement of which strongly correlates to the respiratory cycle of the patient. However, because the neurostimulator will typically be implanted in the upper chest portion of the patient away from these anatomical structures, one or more leads must be used to implant the sensor(s) within these anatomical structures remote from the neurostimulator, thereby requiring additional surgical time and effort.

Systems and methods are described herein that selectively stimulate the fascicles of the HGN 12 at the proximal position 22 of the HGN 12 that innervate the genioglossus 18 and/or the geniohyoid muscles 20, while synchronizing the stimulation with the respiratory cycle of the patient without the need to implant sensor(s) remotely from the neurostimulator.

Figure 2:
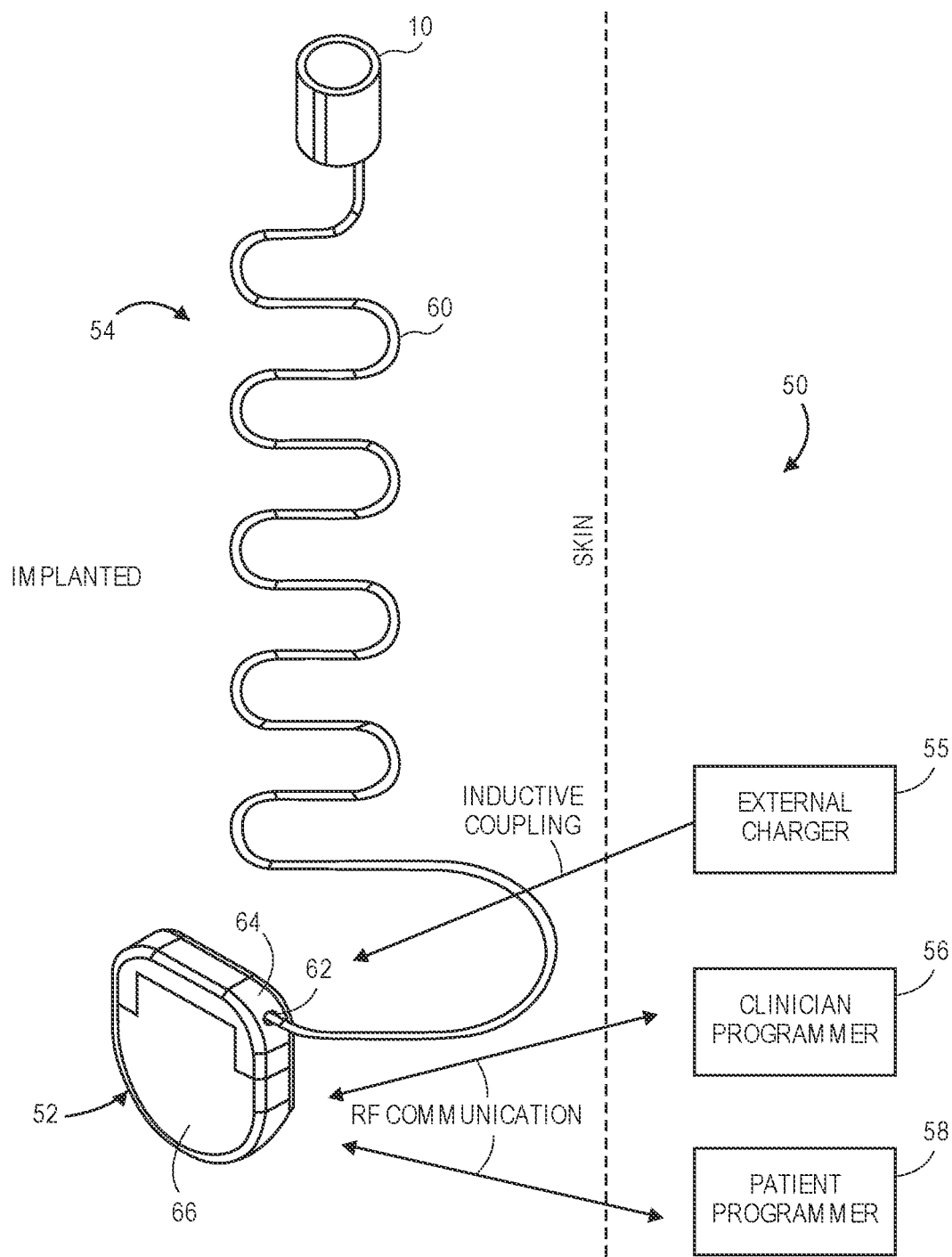
FIG. 2 is a plan view of a stimulation system constructed in accordance with one embodiment of the present inventions.

Referring to FIG. 2, one embodiment of a stimulation system 50 that selectively stimulates the fascicles of the trunk 14 of the HGN 12 that innervate the tongue protrusor muscles for treating obstructive sleep apnea (OSA) will now be described. The system 50 generally comprises an implantable device 52, an electrode lead 54, an external charger 55, a clinician programmer 56, and a patient programmer 58. The electrode lead 54 and the implantable device 52, or alternatively, an implantable pulse generator ("IPG") or a "neurostimulator," can be implanted within a patient. In this patent disclosure we will use terms "IPG" and "neurostimulator", equivalently.

The electrode lead 54 comprises the aforementioned nerve cuff electrode 10 and a lead body 60 coupling the nerve cuff electrode 10 to the implantable device 52 via a proximal lead connector 62 and a corresponding connector receptacle 64. Although the lead body 60 can be straight, in the illustrated embodiment, the lead body 60 may have one or more S-shaped sections in order to provide strain relief, thereby accommodating body movement at the location where the lead body 60 is implanted. This strain relief feature is advantageous, since the lead body 60 is intended to be implanted in a body location such as the neck, where the lead body 60 is subjected to frequent movement and stretching. Thus, the S-shape of the lead body 60 can help prevent damage to the HGN trunk 14, resulting from sometimes, unavoidable pulling of the nerve cuff electrode 10 as a result of neck movements. As will be described in further detail, the nerve cuff electrode 10 comprises an array of circumferentially disposed electrode contacts.

Although only a single electrode lead 54 is shown in FIG. 2, some embodiments of the present system may have an IPG 52 having two receptacles 64 (not shown) for attaching two electrode leads, each electrode lead having a nerve cuff electrode 10. In such a two-electrode lead system, each nerve cuff electrode 10 can be implanted bilaterally to each of the HGN trunks 14. However, it has been determined that only a single nerve cuff electrode 10 implanted at the HGN trunk 14 on either side (unilaterally) can provide sufficiently effective stimulation to protrude the tongue to control OSA. A unilateral stimulation system is advantageous, since it is simpler in numbers of components used and requires only half the surgery to implant only a single nerve cuff electrode 10, instead of two.

The IPG 52 comprises an outer case 66 for housing the electronic and other components (described in further detail below). In one embodiment, the outer case 66 may comprise an electrically conductive, biocompatible material, such as titanium or titanium alloy, and form a hermetically sealed compartment wherein the internal electronics are protected from the body tissue and fluids. In some cases, the outer case 66 may serve as an electrode. As briefly discussed above, the IPG 52 further comprises a receptacle 64 to which the proximal end of the lead body 60 mates in a manner that electrically couples the nerve cuff electrode 10 to the internal electronics (described in further detail below) within the outer case 66.

Figure 3:
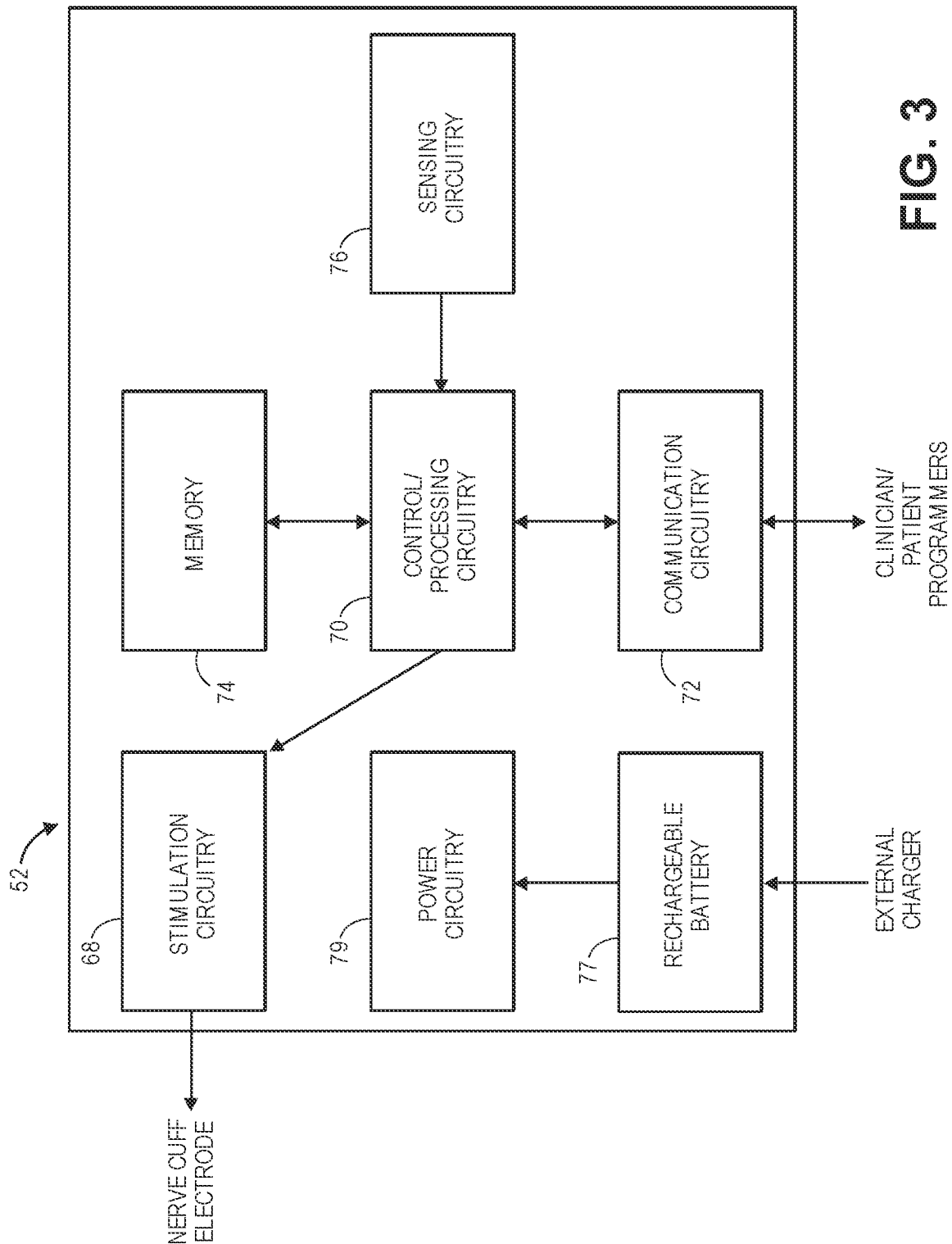
FIG. 3 is a block diagram of the internal components of an implantable pulse generator of the stimulation system of FIG. 2.

Referring now to FIG. 3, the components and circuitry housed in the outer case 66 comprise stimulation circuitry 68, control circuitry 70, communication circuitry 72, memory 74, sensing circuitry 76, a rechargeable power source 77, and power circuitry 79, which all may be conveniently mounted on a printed circuit board (PCB) (not shown).

In one embodiment, the sensing circuitry 76 comprises one or more sensor(s) (not shown) that are contained in the outer case 66 or otherwise attached as an integral part of the IPG 52, such as affixed to the exterior of the outer case 66. Further details on incorporation of sensors within or on the outer case of an IPG 52 are described in U.S. patent application Ser. No. 15/374,538, entitled "Implantable Pressure Sensors and Medical Devices" (now abandoned), which is expressly incorporated herein by reference. In other alternative embodiments, the sensor(s) can be positioned at a site remote from the IPG 52 coupled by a connecting lead, e.g., as described in U.S. patent application Ser. No. 15/093,495, entitled "Upper Airway Stimulator Systems for Obstructive Sleep Apnea" (now abandoned), which is expressly incorporated herein by reference, although as can be appreciated, this would require additional surgery and time to implant the sensing lead.

The sensing circuitry 76 is used primarily to sense the respiration cycle and can, in embodiments of the invention, determine a projected onset of the inspiratory phase of the breathing cycle, or alternatively, may determine the projected onset of the expiratory phase of the breathing cycle. In particular, the sensing circuitry 76 is configured for detecting physiological artifacts that are caused by respiration (e.g., movement or expansion of ribcage and/or abdomen), which are proxies for respiratory phases, such as inspiration and expiration or, if no movement occurs, to indicate when breathing stops. For example, the sensing circuitry 76 may sense movement of the thoracic cavity and/or detect changes in pressure/force in the thoracic cavity. Thus, the sensing circuitry 76 is configured for acquiring, conditioning, and processing signals related to respiration. The sensor(s) of the sensing circuitry 76 can take the form of, e.g., inertial sensors (e.g., accelerometers or gyroscopes), pressure sensors, bioimpedance sensors, ECG electrodes, temperature sensors, GPS sensors, or some combination thereof.

The stimulation circuitry 68 is coupled to the nerve cuff electrode 10 via the lead body 60, and is configured for delivering stimulation to the HGN trunk 14 via selected ones of the electrode contacts 82. The control circuitry 70 is coupled to the stimulation circuitry 68 and controls when, and for how long, the stimulation circuitry 68 applies stimulation to the HGN trunk 14. The control circuitry 70 may also control the intensity of the stimulation applied by the stimulation circuitry 68 to the HGN trunk 14, e.g., by varying the amplitude, pulse width, or frequency of the stimulation.

As will be described in further detail below, the control circuitry 70 may select the optimal electrode contact(s) of the nerve cuff electrode 10 used for stimulating the HGN trunk 14, and in particular, the electrode contact(s) that stimulate the fascicles of the HGN 12 innervating the tongue protrusor muscles, e.g., the genioglossus 18 or geniohyoid 20 muscles, to thereby prevent or alleviate obstructive apneic events. However, stimulation of nerve fascicles innervating the tongue retractor muscles, e.g., the hyoglossus 26 and styloglossus muscles 28, as well as the intrinsic muscles of the tongue 16, should be avoided to the extent possible.

The memory 74 is configured for storing specific data gathered by the sensing circuitry 76 and programming instructions and stimulation parameters. The control circuitry 70 may recall the sensed data from the memory 74 and analyze it to determine when stimulation should be delivered to the HGN trunk 14 to synchronize the stimulation delivery with the respiratory cycle. In some embodiments, the sensor data may be analyzed to predict the onset of the next inspiratory phase of the breathing cycle and to deliver stimulation right before, at, or slightly after the predicted onset of the inspiratory phase.

Thus, when the patient is in the inspiratory portion of the respiratory cycle—where the patient is breathing in or attempting to breath in, the control circuitry 70 may, in some embodiments, apply stimulation, thereby causing forward displacement of the tongue, and causing the upper airway to remain un-obstructed during inspiration while sleeping. The control circuitry 70 causes the stimulation circuitry 68 to apply stimulation during these inspiratory phases of the respiratory cycle (or applying stimulation starting slightly before the inspiration and ending at the end of inspiration), and not the remainder of the respiration cycle, when all other conditions for stimulation are met.

The IPG 52 may be toggled between an ON position and an OFF position using one of a variety of techniques. In one embodiment, the IPG 52 may have a magnetic reed switch (not shown) contained within the outer case 66 that can sense a magnetic field from an external magnet. An external magnet may be used to toggle the IPG 52 to the OFF position or alternatively to an ON position. Oftentimes, patients may need to undergo an MRI scan. A reed switch in the IPG 52 may make it MRI incompatible. In another embodiment, the IPG 52 may have a sensor (not shown) that is sensitive to movement (i.e., a motion detector), such as an inertial sensor (e.g., an accelerometer or gyroscope), and a switch that can be toggled between a closed state and an open state to place the implanted IPG 52 between an ON position and an OFF position by tapping the implanted IPG 52 with the hand. For example, one tap may switch the IPG 52 from an ON position to an OFF position, and another tap may switch the IPG 52 from an OFF position to an ON position. In one preferred embodiment, the same sensing circuitry 76, along with the sensor, that is used for detecting physiological artifacts that are caused by respiration, may be used to sense the tapping of the implanted IPG 52 to toggle the IPG 52 between the ON position and the OFF position.

In another preferred embodiment, the IPG 52 can be toggled between an ON position and an OFF position in response to multiple quick successive taps (e.g., less than a second between taps), as opposed to a single tap, which may occur by accidental bumping and cause an inadvertent turn off of the IPG; for example, two taps to switch the IPG 52 from an ON position to an OFF position, and two taps to switch the IPG 52 from an OFF position to an ON position. As a redundancy, the patient programmer 58 or the clinician programmer 56 may also be configured to be able to toggle the IPG 52 from ON to OFF and from OFF to ON.

In an optional embodiment, the sensing circuitry 76 comprises a body position sensor (not shown) (e.g., an inertial sensor) configured for measuring an orientation of the patient's body. In this case, the control circuitry 70 determines the orientation of the patient's body, and activates the portions of the sensing circuitry 76 that monitor the physiological artifacts that are caused by respiration when the orientation indicates that the patient is in an apneic position (i.e., a position in which the patient is likely to experience apneic events). The most common apneic position is supine, but can include left side, right side, or both. Patients with positional sleep apnea experience significantly more apneic events while in particular apneic positions, thereby allowing the neurostimulator 52 to preserve battery life by monitoring the physiological artifacts that are caused by respiration only when the patient is likely to experience apneic events. The memory 74 may store positional sleep apnea data for the patient that can be consulted by the control circuitry 70 when determining whether the patient is in an apneic position.

In another optional embodiment, the sensing circuitry 76 comprises a sleep sensor (not shown) configured for measuring a physiological parameter indicative of whether the patient is sleeping. The sleep sensor may comprise sensors used in polysomnography, such as an EMG sensor across the jaw line, an EEG sensor, and an EOG sensor, an inertial sensor, or a temperature sensor. In this case, the control circuitry 70 determines whether the patient is asleep, and activates the portions of the sensing circuitry 76 that monitor the physiological artifacts that are caused by respiration only when the patient is asleep. This preserves battery life since sensing and monitoring only occurs when the patient is actually asleep.

Further details describing the use of body orientation and sleep sensors are discussed in U.S. patent application Ser. No. 15/093,627, entitled "Upper Airway Stimulator Systems for Obstructive Sleep Apnea" (now abandoned), which is expressly incorporated herein by reference.

The communication circuitry 72 is configured for wirelessly communicating transcutaneously (through the patient's skin) with the clinician programmer 56 and patient programmer 58 using radio frequency (RF) signals, e.g., via an Off The Shelf (OTS) Inductive/Bluetooth/MICS radio link. The communication circuitry 72 may include one or more AC coils for transmitting and receiving the RF signals to and from the clinician programmer 56 and patient programmer 58.

The rechargeable power source 77, for example, a rechargeable battery, and power circuitry 79 are configured for providing operating power to the IPG 52. The rechargeable power source 77 may comprise a lithium-ion or lithium-ion polymer battery, and provide an unregulated voltage to the power circuitry 79. The power circuitry 79, in turn, generates regulated or unregulated voltage to the various circuits located within the IPG 52. The rechargeable power source 77 is recharged using rectified AC power received by an AC receiving coil (such as one of the coils coupled to the communication circuitry 72) from the external charger 55. The AC magnetic field emitted by the external charger 55 induces AC currents in the AC receiving coil (not shown), which is rectified by circuitry (not shown) that rectifies the AC current to produce DC current that is used to charge the power source 77.

Referring back to FIG. 2, to recharge the IPG 52, the external charger 55 or a part of the charger having a coil, which generates the AC magnetic field, is placed against, or otherwise adjacent, to the patient's skin over the implanted IPG 52. The clinician programmer 56 may be used to transcutaneously communicate with the implanted IPG 52 for programming the IPG 52 and querying the IPG 52 for status. For example, the clinician programmer 56 can be used to configure certain programs and processes used by the control circuitry 70 in the IPG 52 to determine when the stimulation pulses are to be delivered to electrode contacts of the nerve cuff electrode 10. The clinician programmer 56 can also be used to program specific stimulus parameters, such as stimulus pulse width, stimulus frequency, duration of a train pulses and pulse amplitude. The amplitude may be expressed in current, for example, milliamperes, or it could be expressed in volts, such as 0.3 volts. The choice between milliamperes or volts to express stimulus amplitude will depend on whether the design of the stimulation circuitry 68 provides stimulus pulses that are constant voltage or constant current. Another important function of the clinician programmer 56 is the ability to select modes of stimulation. For example, the IPG 52 may operate in a monopolar stimulation mode (also sometimes referred to as a "unipolar" mode) and in a bipolar stimulation mode.

As used in this present disclosure, a monopolar stimulation mode means that one of the electrode contacts used is at least a portion of the outer case 66 that will function as an indifferent/anode electrode. The indifferent electrode is part of the electrical circuit with at least one electrode contact of the nerve cuff electrode 10 as the active/cathode electrode contact that stimulates the HGN trunk 14. Generally, that part of the outer case 66 that is acting as the indifferent electrode does not stimulate any tissue or nerve, but merely functions as a return electrode and may be a biocompatible, conductive metal such as a titanium alloy, as discussed above.

A bipolar stimulation mode means, for purposes of this disclosure, that the outer case 66 is not part of the stimulation circuit. At least two electrode contacts of the nerve cuff electrode 10 must be selected and will be part of the bipolar mode electrical stimulation circuit. Sometimes a stimulation circuit can have three or even more electrode contacts functioning together. This may also be referred to as "bipolar" stimulation mode even though there are sometimes more than two active electrode contacts in the stimulation circuit. Sometimes a three-electrode contact system may be referred to as a tripolar circuit. For purposes of this disclosure and application, we will consider a three or more electrode-contact stimulation circuit (if it excludes the outer case 66) as variants of a bipolar stimulation mode and will be included as within a "bipolar" stimulation mode. The present stimulation system in its various embodiments, thus, may operate in either monopolor or bipolar stimulation modes.

Significantly, to facilitate selective stimulation of the fascicles of the HGN 12 that innervate the tongue protrusor muscles, the clinician programmer 56 also selects which electrode contacts of the nerve cuff electrode 10 or the indifferent electrode of the outer case 66 are to be in the stimulation circuit. The clinician programmer 56 may also be able to query the status of the IPG 52 for a number of status functions, such as battery status. Another query may be whether the IPG 52 is in an ON position or an OFF position. In the ON position, the stimulation circuitry 68 within the IPG 52 is enabled and stimulation pulses can be delivered via the selected electrode contact or contacts of the nerve cuff electrode 10. When the patient is awake, the IPG may be placed automatically or by choice into the OFF position or mode, and the stimulation circuitry 68 is not enabled and no stimulation can occur.

The patient programmer 58 offers more limited programming options than the clinician programmer 56. The patient programmer 58 may provide the option to toggle the IPG 52 into the OFF position or into the ON position. Also, the stimulus pulse amplitudes may be adjusted for a limited range of up and down. Often the patient programmer 58, because of limited functionality, may be in a package or form that is much smaller in size than the clinician programmer 56. The clinician programmer 56 and patient programmer 58 may take the form of commercial electronic smart devices on which there are installed customized applications for performing the afore-described functions.

Figure 4:
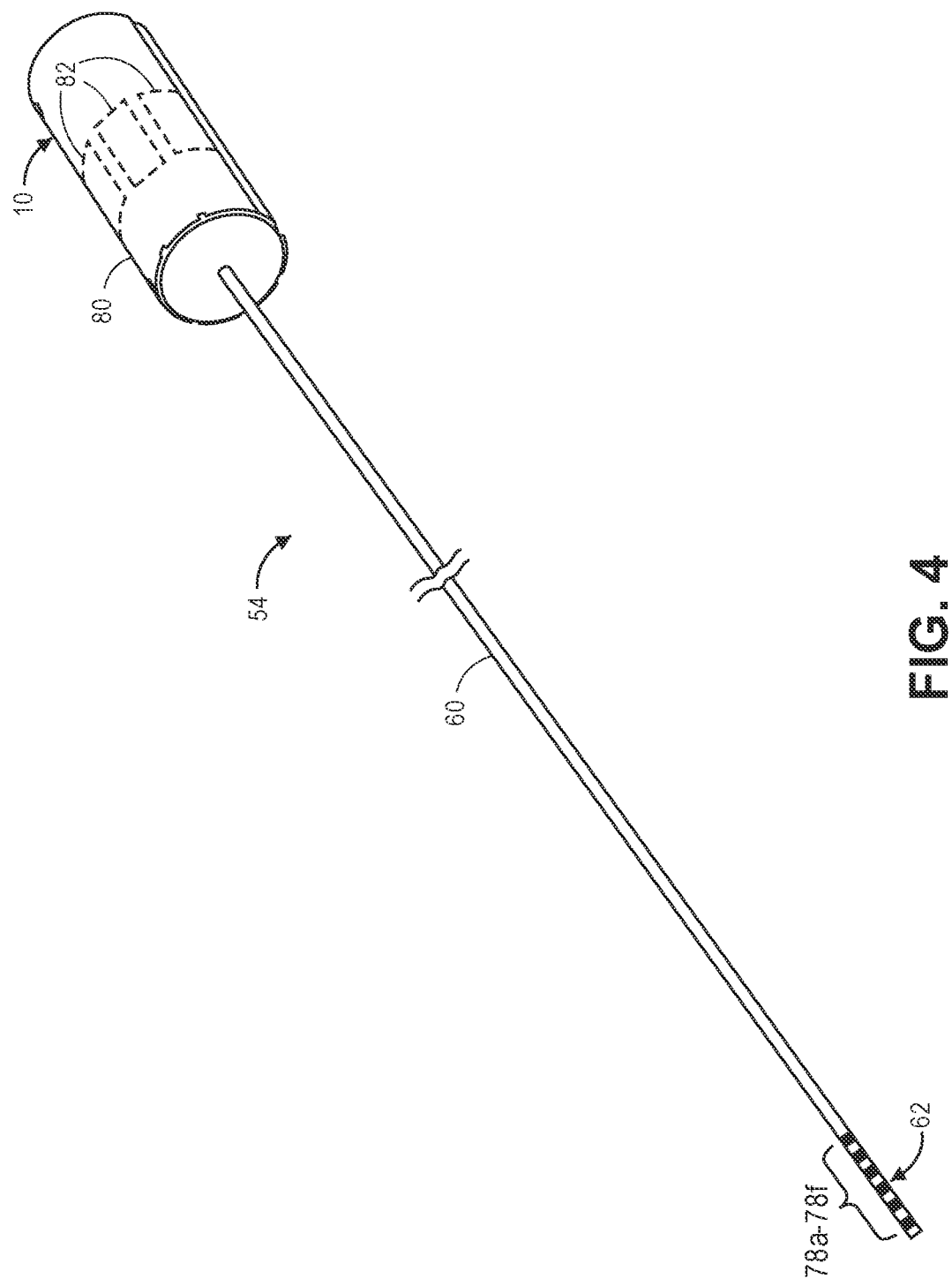
FIG. 4 is a perspective view of a lead electrode that may be used in the stimulation system of FIG. 2.
Figure 5:
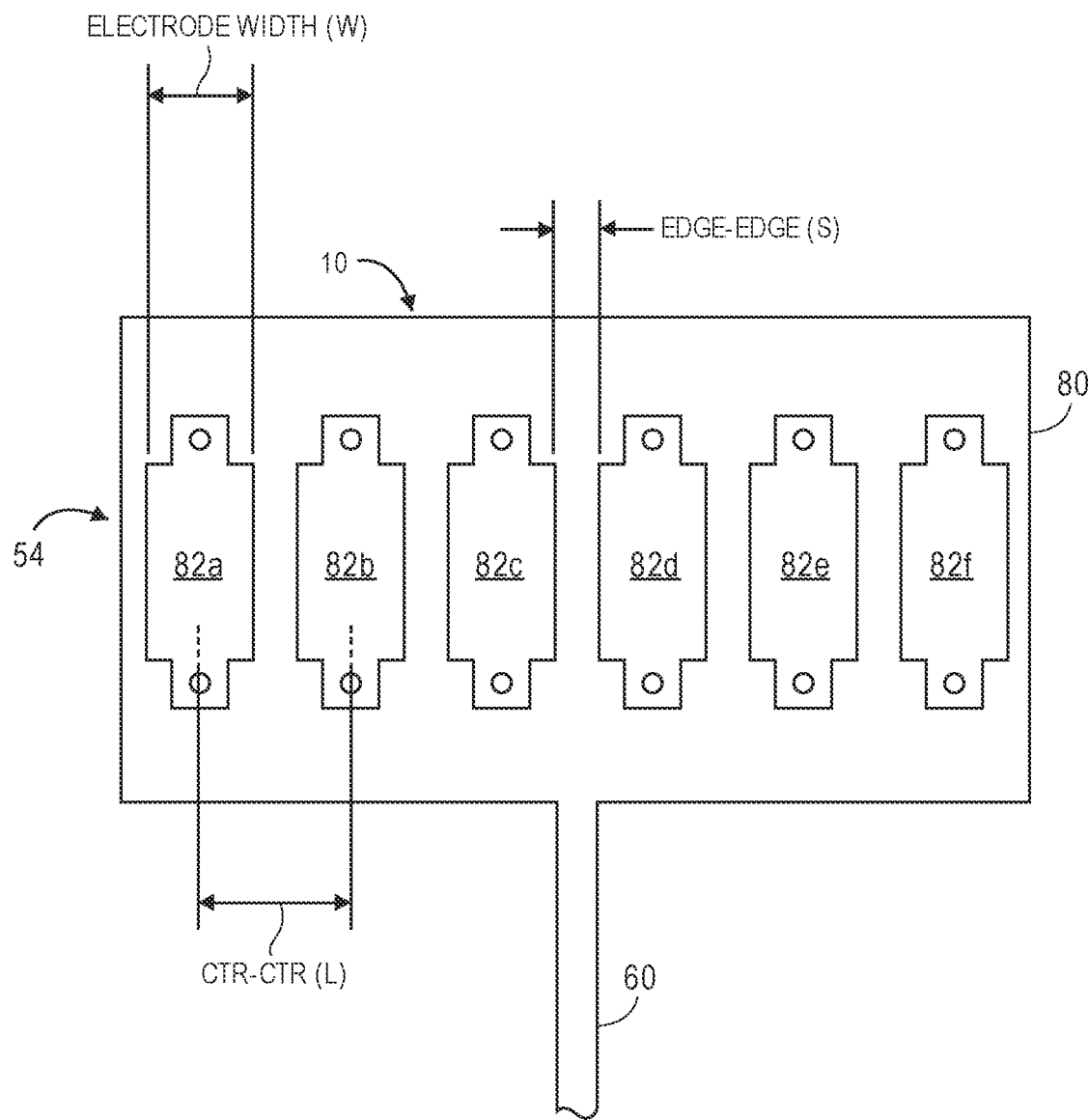
FIG. 5 is a plan view of a nerve cuff electrode of the lead electrode of FIG. 4, particularly shown in an unfurled state.
Figure 6:
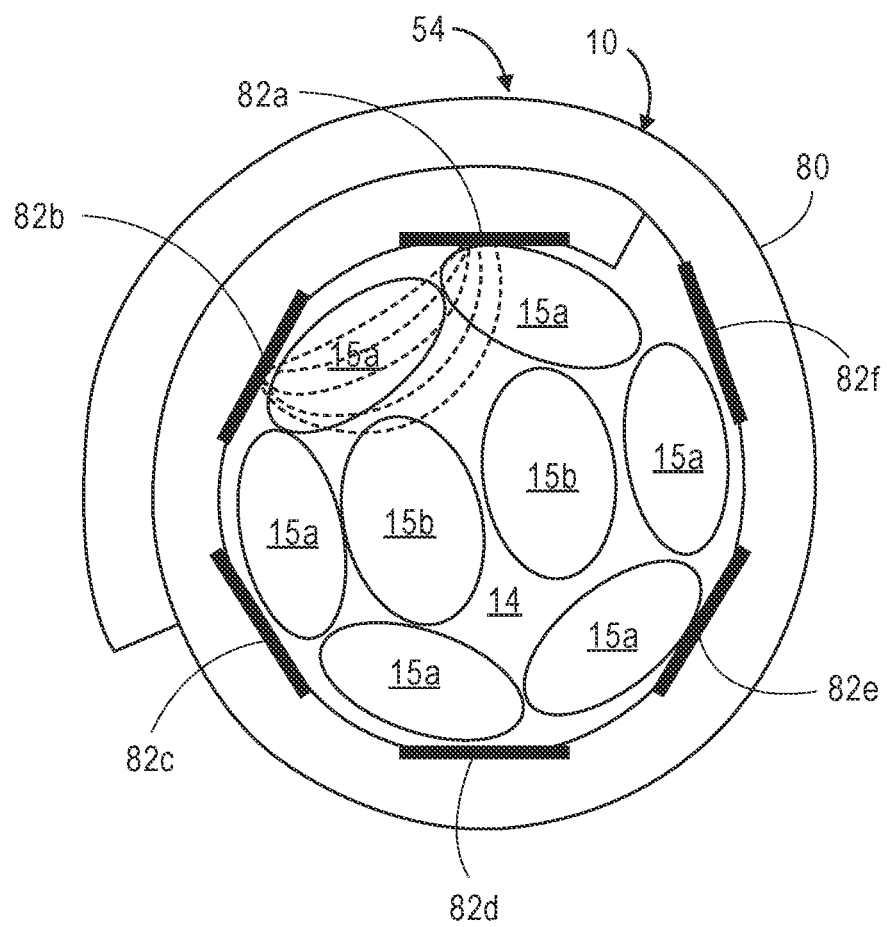
FIG. 6 is a cross-sectional view of the nerve cuff electrode of FIG. 5, particularly shown in a furled state.

Referring now to FIGS. 4-6, an embodiment of an electrode lead 54 that may be used in the stimulation system will now be described in further detail. The proximal lead connector 62 comprises a linear array of connector contacts 78a-78f (in this case, six) for connecting to the connector receptacle 64 of the IPG 52 when the proximal lead connector 62 is inserted into the connector receptacle 64.

The nerve cuff electrode 10 further comprises a nerve cuff body 80 that is capable of substantially or completely encircling the HGN trunk 14. The nerve cuff electrode 10 may be, in some embodiments, manufactured to be self-curling, and may be designed to self-adjust in accordance with the diameter of the HGN trunk 14. The material used for the electrode substrate can be typical implantable electrode materials, such as silicone, polyurethane or other less conventional implant materials, e.g., liquid crystal polymers. The material consistency of the formed cuff body 80 should be pliable enough to allow the clinician to unfold the cuff, as shown in FIG. 5, and placed around the HGN trunk 14 and to have the nerve cuff electrode 10 curl back around itself, as shown in FIG. 6. Although FIG. 5 illustrates the lead body 60 in the middle of the cuff body 80, the lead body 60 can be positioned at either the left or right end of the cuff body 80, and the lead body 60 may even point 90 degrees from the direction the lead body 80 is aligned as shown in FIG. 5. The substrate material of the nerve cuff body 80, therefore, should have a memory property to the extent that it will tend to return to its original curled shape. In one advantageous manufacturing process, the nerve cuff electrode 10, lead body 60, and proximal lead connector 62 may be constructed of a flexible circuit, as described in U.S. patent application Ser. Nos. 15/634,057 and 15/634,134, both entitled "Nerve Cuff Electrodes Fabricated Using Over-Molded LCP Substrates" (now abandoned), which are expressly incorporated by reference.

The nerve cuff electrode 10, as shown, will also have some give, so that if the nerve swells during the inflammatory phase post-surgery, the inner lumen size of the nerve cuff electrode 10 can expand and accommodate to the nerve swelling. This capability of self-adjustment over time is important because once tissue has been dissected from around the nerve, there often will be an inflammatory response around the damaged tissue and also in response to the presence of foreign matter that may be introduced during the surgical implantation of the nerve cuff electrode 10. Indeed, the nerve cuff electrode 10, itself, is likely seen as a foreign matter contributing to inflammation. The inflammatory response may be ongoing over a period of months. During this period, the nerve, itself, may swell up and increase substantially in diameter, perhaps up to 50% more than before the surgery. Once past this inflammatory response, the nerve diameter may then decrease in size, closer to its original diameter. If the inner lumen size of the nerve cuff electrode 10 does not adjust in size to accommodate the increase in the nerve diameter, constriction of the target nerve can result in traumatic cell damage and nerve death. Further details describing various self-expanding nerve cuff electrodes are set forth in U.S. Provisional Patent Application Ser. No. 62/500,080, entitled "Nerve Cuff Electrode Locking Mechanism," and U.S. Provisional Patent Application Ser. No. 62/500,091, entitled "Self-Expanding Nerve Cuff Electrode," which are both expressly incorporated herein by reference.

The nerve cuff electrode 10 further comprises an array of electrode contacts 82a-82f (in this case, six) affixed to an inner surface of the cuff body 80 (when furled), such that when the cuff body 80 encircles the HGN trunk 14, the electrode contacts 82a-82f are in contact with the HGN trunk 14. To facilitate selective activation of the fascicles of the HGN trunk 14 that innervate the protrusor muscles, the electrode contacts 82 are affixed to the cuff body 80 in a manner, such that when the cuff body 80 encircles the HGN trunk 14, the electrode contacts 82 are circumferentially disposed about the HGN trunk 14. In this case, the electrode contacts 82 span the cuff body 80 circumferentially around the HGN trunk 14. The electrode contacts 82a-82f preferably circumferentially span at least a 180-degree arc of the HGN trunk 14, and more preferably span at least a 270-degree arc of the HGN trunk 14, so that any fascicle within the HGN trunk 14 can be selectively stimulated by delivering stimulation energy from the electrode contact or contacts 82 adjacent to the fascicle, as described in further detail below. To facilitate coverage of all of the fascicles, the number of electrode contacts 82 preferably equals at least three, and more preferably, at least six. The electrode contacts 82 are also aligned on the inner surface of the cuff body 80, such that, when the cuff body 80 encircles the HGN trunk 14, the electrode contacts 82 are axially aligned with each other. For the purposes of this specification, electrode contacts 82 are axially aligned with each other if they lie in the same plane that is perpendicular to the axis of the cuff body 80 or axis of the HGN trunk 14. In addition, although FIG. 5 shows an embodiment of cuff having electrode contacts aligned in a single row, in other embodiments, it is possible to construct a cuff having two or even more parallel rows of electrode contacts (not shown) that are parallel to the direction defined by electrode contacts 82a-82f. The latter electrode contact arrangement(s) will provide an additional degree of freedom in stimulating a target nerve fascicle.

Although the exemplary nerve cuff electrode 10 comprises six electrode contacts 82a-82f, other nerve cuff electrodes may have two to five electrode contacts 82 or more than six electrode contacts 82. The preferred range, however, of the numbers of electrode contacts 82 on any particular nerve cuff electrode is between three to eight electrode contacts 82, so as to surround the circumference of the HGN trunk 14, and provide a sufficient number of independent electrode channels from which to select and to recruit the protrusor muscles without recruiting the retractor muscles. The connector contacts 82a-82f are respectively and independently electrically coupled to the electrode contacts 82a-82f via electrical conductors (not shown), such that the electrode contacts 82a-82f may be independently activated in either monopolar stimulation mode or bipolar stimulation mode. In the monopolar stimulation mode, one or more of the electrode contacts 82a-82f will preferably be activated as cathode(s), whereas in the bipolar stimulation mode, one or more of the electrode contacts 82a-82f will be activated as cathode(s), and one or more other electrode contacts 82a-82f will be activated as anode(s).

Although in some embodiments, the nerve cuff electrode 10 may be operated in a monopolar stimulation mode, requiring that only one electrode contact 82 of the nerve cuff electrode 10 be activated at any given time, as will be described in further detail below, it is desirable that the nerve cuff electrode 10 be operated in a bipolar stimulation mode to facilitate selective recruitment of the fascicles 15 in the HGN trunk 14, requiring that at least two electrode contacts 82 of the nerve cuff electrode 10 be activated at any given time.

That is, monopolar stimulation results in a more diffuse electrical field that will tend to recruit most fascicles 15 in the HGN trunk 14 including those unwanted fascicles, whereas bipolar stimulation results in a more specific and confined electrical field that will tend to recruit only the targeted fascicles 15 in the HGN trunk 14. Thus, the fascicles 15 in the HGN trunk 14 that innervate the tongue protrusor muscles can be more selectively activated via bipolar stimulation. Because the electrode contacts 82 will circumferentially surround the HGN trunk 14, the electrical field generated by the nerve cuff electrode 10 in the bipolar stimulation mode can be selectively steered around the HGN trunk 14 to recruit the desired fascicles 15 within the HGN trunk 14. It is further noted that, because the fascicles 15 innervating the tongue protrusor muscles sometimes, depending on the individual anatomy, may be more peripherally located within the nerve bundle that is located at the proximal position 20 to the HGN branches 24, it is desirable that adjacent electrode contacts 82 can be activated in the bipolar arrangement, such that the electrical field extends only peripherally into the HGN trunk 14.

Thus, with reference to FIG. 6, it may be desirable to activate electrode contact pair 82a-82b, electrode contact pair 82b-82c, electrode contact pair 82c-82d, electrode contact combination 82d-82e, electrode contact combination 82e-82f, or electrode combination 82f-82a. As shown in FIG. 6, electrode combination 82a-82b, when activated, create a confined bipolar electrical field therebetween that recruits one or more of the peripheral, less centrally located fascicles 15a, as opposed to recruiting the more centrally located fascicles 15b. Of course, any of the other electrode contact combinations can be operated in a bipolar manner to recruit other peripherally located fascicles 15a. The first one of the electrode contacts 82 in the combination can be a cathode, and the second one of the electrode contacts 82 in the combination can be an anode, or vice versa. There are other possible electrode contact combinations or contact sets that can be possibly chosen, which are described later in this disclosure in relation to titrating and fitting electrode contacts to determine the optimal set(s).

Notably, the strongest electrical field generated by the nerve cuff electrode 10 will be beneath an active electrode contact/cathode. Thus, in order to effectively employ bipolar stimulation, the nerve cuff electrode 10 may have the following design constraint: L≤2W, where W is the width of each electrode contact 82, and L is the center-to-center distance between two adjacent electrode contacts 82, as illustrated in FIG. 5. This constraint is based on the commercial needs in neuromodulation therapies to cover the most distance with spatial separations L and using the fewest number of electrode contacts 82. The width of the electrode contacts 82 will typically be based on the particular neural element that will be stimulated or the size of the cuff body 80, or a combination thereof, and will set the strength ranges of the electric fields generated by the nerve cuff electrode 10. As the center-to-center distance L exceeds the L≤2W design constraint, the electric field generated by a bipolar pair of electrode contacts 82 quickly starts to resemble a monopolar electric field as if there was a remote anode (unless there is a dramatic increase in the electric field amplitude). The ability to perform current steering between two or more adjacent electrode contacts 82 also weakens. In contrast, if adjacent electrode contacts 82 are too close or touching each other, there may be bleeding of electrical fields across the active contacts 82 at a higher amplitude, thereby creating a short that reduces the ability to spatially select fascicles. Thus, it is important that the center-to-center distance L between adjacent electrode contacts 82 and the width W of the electrode contacts 82 be constrained.

To maintain the distance between the electrode contacts 82a, 82f in accordance with the L≤2W design constraint over a variety of different nerve sizes, thereby ensuring that bipolar stimulation using the electrode contacts 82a, 82f is effective, the nerve cuff electrode 10 may optionally be designed in the manner described in U.S. Provisional Patent Application Ser. No. 62/552,266, entitled "Stimulator Systems and Methods or Selectively Recruiting Fascicles in Hypoglossal Nerve Trunk," which is expressly incorporated herein by reference.

The stimulation energy generated by the stimulation circuitry 68 takes the form of a train of electrical pulses under control of the control circuitry 70. The electrical pulse train may be set to a constant time duration or it may be adaptive, meaning that duration of the train of pulses can change dynamically based on a predictive algorithm that determines the duration of the inspiratory phase of the respiratory cycle.

Referring now to FIG. 7, various electrical pulse trains that can be generated by the stimulation circuitry 76 will now be described. In one embodiment illustrated in FIG. 7a, an electrical pulse train comprises a single stimulation pulse S1 or S2. The stimulus pulse S1 or S2 has stimulus parameters: stimulus pulse width, the stimulus pulse current or voltage amplitude, and stimulus frequency. The frequency determines the time duration between two consecutive pulses S1, S2. These multiple stimulus pulses may also be called a "train" of pulses or a "burst" of pulses. Usually there is a quiescent period, as shown in FIG. 7d, between two trains or burst of stimulus pulses, in this case, between stimulation pulses S6-S9 and S10. During this quiescent time, there is no stimulation occurring. The stimulus pulses can be cathodic (upper Y-axis direction in FIG. 7) or anodic (lower Y-axis direction in FIG. 7). The stimulus could be bi-phasic, and symmetric (FIG. 7b), meaning the electrical charge in the cathodic direction and anodic direction of a single pulse S3 are the same. Sometimes stimulation pulses S4, S5 can be bi-phasic, charge-balanced, but not symmetric (FIG. 7c). The cathodic amplitude is greater than the anodic amplitude, but the total charge delivered out through an electrode contact during the cathodic phase is balanced by the same quantity of electrical charge incoming into the same electrode contact. Area C equals area D and area E is equal to area F. A stimulus that is charge-balanced is desirable in order to ensure that the electrode contacts do not erode prematurely during chronic implantation. For example, a charge-unbalanced cathodic pulse as shown in FIG. 7a can stimulate a nerve, but is not a desirable stimulus choice for an IPG. Although it is possible to elicit nerve stimulation using an anodic pulse, a cathodic pulse is generally used to stimulate a nerve, since the nerve stimulation threshold (stimulus amplitude that just triggers nerve conduction) needed is much lower with a cathodic pulse than an anodic pulse.

Figure 8:
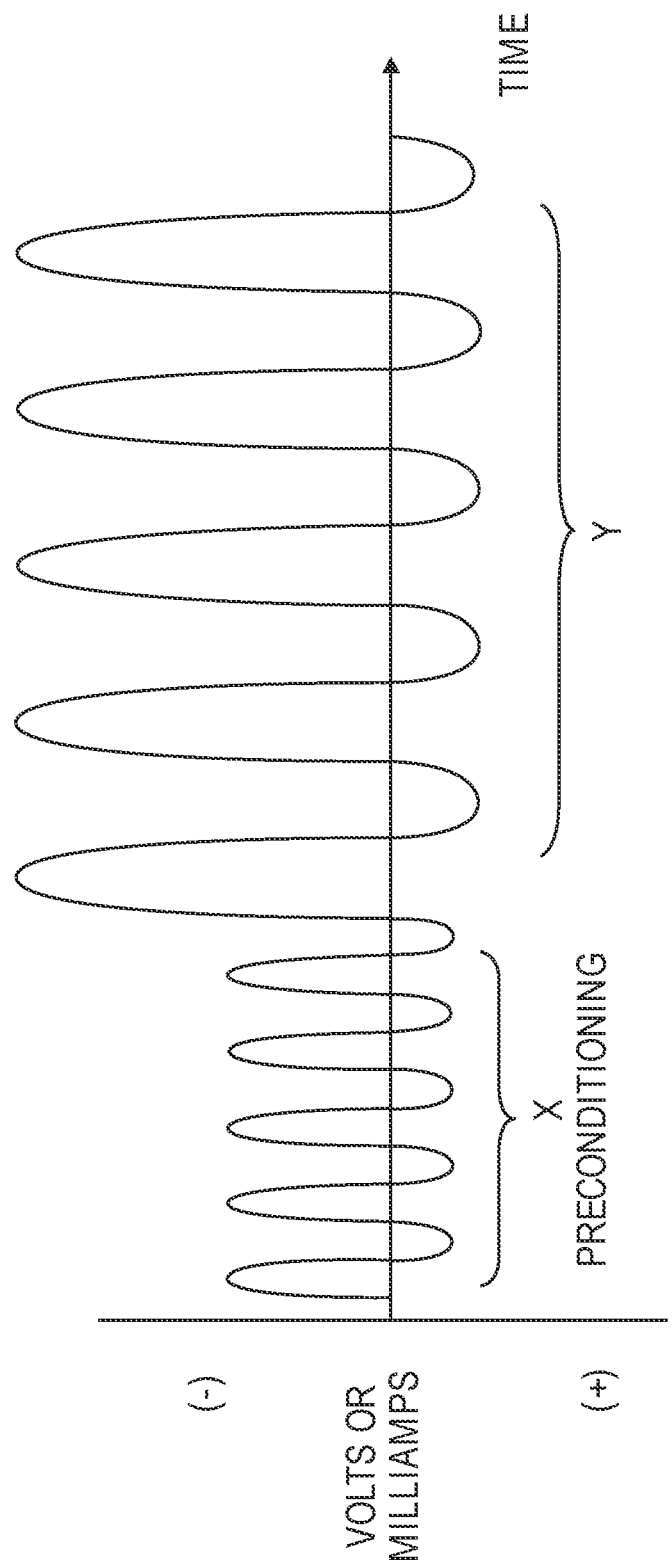
FIG. 8 is a diagram of a pre-conditioning electrical pulse train that can be generated by the stimulation system of FIG. 2.

Referring now to FIG. 8, shows a train of biphasic, charge-balanced pulses comprising initial pre-conditioning pulses, designated by X, followed by larger amplitude stimulus pulses, designated by Y, which are at a higher amplitude compared to the pre-conditioning pulses. Both X and Y stimuli may be charge-balanced. The X preconditioning pulses may be as low as 10% and more typically 50-90% of the Y stimulus pulses. This particular stimulation pattern can be used to "precondition" the peripheral, less centrally located nerve fascicles 15a (i.e., the nerve fascicles closer to the outer circumference of the HGN trunk 14) over the more centrally located nerve fascicles 15b (i.e., the nerve fascicles closer to the center of the HGN trunk 14), as shown in FIG. 6. Although it is a general assumption that it is the peripherally located target fascicles 15a that innervate the tongue protrusor muscles, it is dependent on individual anatomy and the target fascicles may in fact be more centrally located in the HGN trunk. Thus, the usefulness of preconditioning will depend on the anatomy of an individual and the location of the target nerve fascicles in relation to the center of the nerve bundle. Preconditioning, as described, is a therefore a stimulation tool that may be optionally applied depending on circumstances.

In operation, the initial pre-conditioning pulses X at the lower amplitude will stimulate the more peripherally located nerve fascicles 15a of the HGN trunk 14. This causes these nerve fascicles to be "pre-conditioned," so that they are not inclined to be stimulated later by a larger amplitude stimulation pulses Y. The lower amplitude pre-conditioning pulses X are low enough in amplitude that they will not stimulate the more centrally located nerve fascicles 15b of the HGN trunk 14. While the peripherally located nerve fascicles 15a of the HGN trunk 14 are in their "pre-conditioned" state and not excitable, the larger amplitude stimulation pulses Y will reach into the center of the HGN trunk 14 with sufficient charge density to stimulate and activate the more centrally located nerve fascicles 15a.

Thus, in the case where the more centrally located nerve fascicles 15b of the HGN trunk 14 happen to innervate the tongue protrusor muscles, this preconditioning stimulation pattern can provide selective stimulation of these centrally located nerve fascicles 15b without stimulating nerve fascicles that innervate other extraneous muscles, namely the peripherally located nerve fascicles 15a. In other embodiments, instead of increasing the stimulus amplitude in the latter part of pulse train Y, another possible way of achieving higher electrical charge intensity to activate the centrally located nerve fascicles 15b of the HGN trunk 14 is to, relative to the pre-conditioning pulses, increase stimulus pulse width, increase frequency of stimulation, or provide some combination thereof. It should be appreciated that the use of the preconditioning stimulation pattern is not limited to HGN trunks 14, but can be used with any nerve trunk where it is desirable to selectively stimulate more centrally located fascicles over more peripherally located nerve fascicles.

Thus, selective targeting of the tongue protrusor muscles can be achieved by spatially stimulating the fascicles innervating these tongue protrusor muscles by selectively using the electrode contacts 82 of the nerve cuff electrode 10 to stimulate the HGN trunk 14. Furthermore, by using lower amplitude pre-conditioning pulses to desensitize the fascicles innervating the tongue retractor muscles, followed by a cathodic stimulation to target the fascicles innervating the tongue protrusor muscles, even better targeting of the tongue protrusor muscles can be achieved in the case where the fascicles innervating the tongue protrusor muscles are deeper in the HGN trunk 14. Thus, it can be appreciated from the foregoing that the combination of several electrode contacts 82 on the nerve cuff electrode 10 that provide multiple independent electrode channels and the pre-conditioning stimulation trains provides a margin for placement of the nerve cuff electrode 10 on the HGN trunk 14 and variation in the surgical approach across various surgeons.

Figure 9:
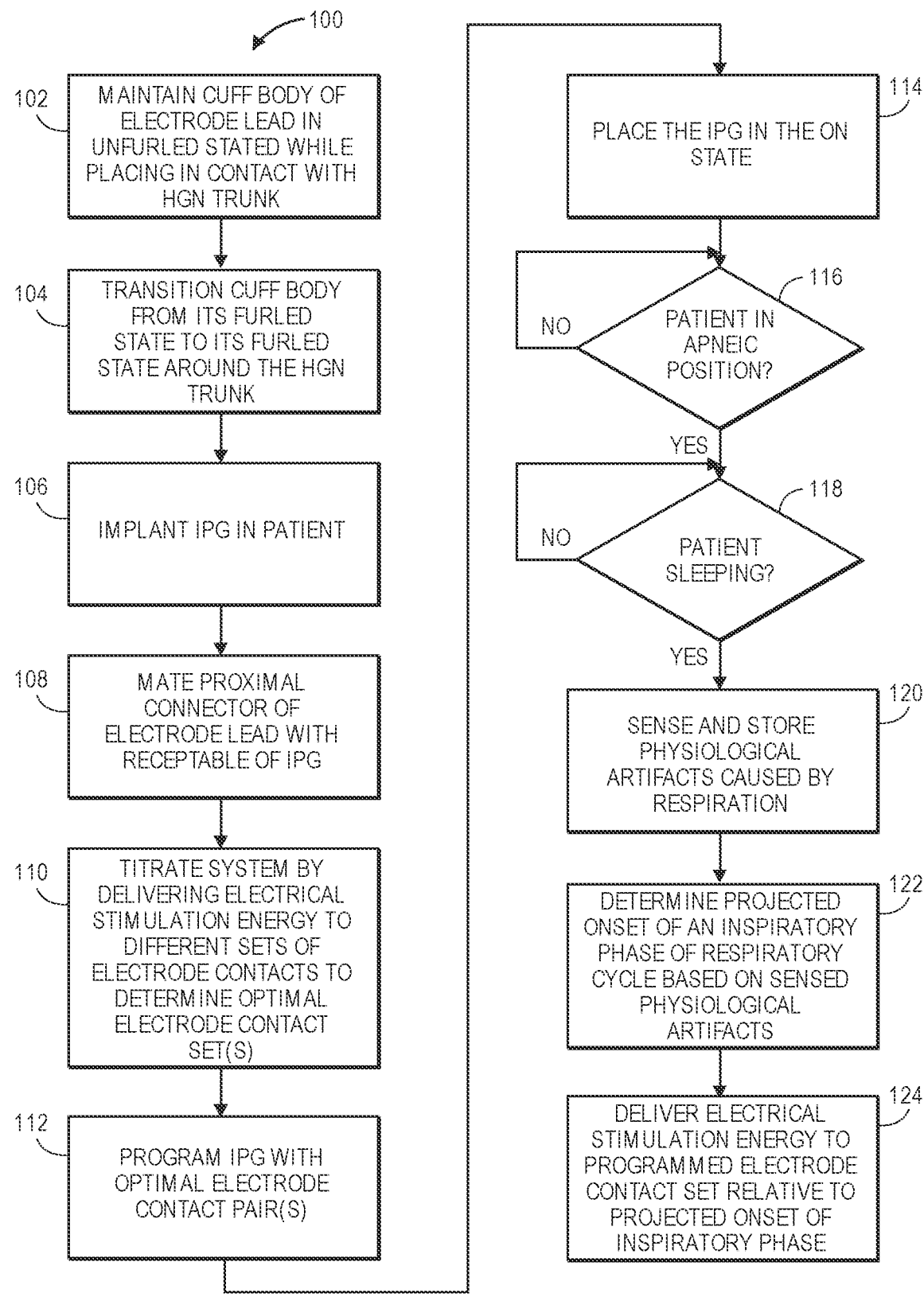
FIG. 9 is a flow diagram illustrating one method of implanting and fitting the stimulation system of FIG. 2 to a patient.

Having described the arrangement and function of the stimulation system 10, one embodiment of a method of using the stimulation system 10 to treat OSA in a patient will now be described with reference to FIG. 9.

First, the electrode contacts 82 are circumferentially disposed around the HGN trunk 14. In particular, the cuff body 80 is maintained in the unfurled state (FIG. 5) while placing the cuff body 80 around the HGN trunk 14 (step 102). For example, the unfurled cuff body 80 may be placed underneath the HGN trunk 14. The cuff body 80 may be maintained in the unfurled state by, e.g., holding it open, although the cuff body will tend to return to its furled, resting state. The HGN trunk 14 may have a diameter, e.g., typically in the range of 2.5 mm to 4.0 mm.

Next, the cuff body 80 is transitioned from the unfurled state into the furled state (FIG. 6), such that the cuff body 80 wraps around the HGN trunk 14 (step 104). The cuff body 80 may be placed from the unfurled state into the furled state by letting go of both ends of the cuff body 80, such that the cuff body 80 automatically transitions from the unfurled state to the furled state. The electrode contacts 82 preferably circumferentially span at least a 180-degree arc around the HGN trunk 14, and more preferably, at least a 270-degree arc around the HGN trunk 14. Preferably, the center-to-center spacing L of each pair of adjacent ones of the electrode contacts 82 is equal to or less than twice the width W of each electrode contact of the respective pair of adjacent electrode contacts 82.

Next, the IPG 52 is implanted within the patient (step 106), and the proximal lead connector 62 is mated with the receptacle 64 of the IPG 52 (step 108). Next, the system 50 is titrated to determine at least one electrode contact 82 (an "electrode contact set") that provides the best treatment of the OSA by delivering electrical stimulation energy to different electrode contact sets 82 to determine the optimal electrode contact set(s) (step 110). For example, electrode contact set 82 may be selected, an electrical pulse train may be delivered to the selected electrode contact set to stimulate the HGN trunk 14, and preferably, the fascicles of the HGN trunk 14 innervating the tongue protrusor muscles, and then repeated for all possible electrode sets to determine the optimal electrode contact set(s). Further details of several techniques for titrating the neurostimulation system 10 are discussed below. In one method, each electrode contact set comprises a pair of adjacent ones of the electrode contacts 82, in which case, the pairs of electrode contacts are selected for delivery of the electrical pulse trains in a bipolar mode. In another method, each electrode contact set comprises a single electrode contact 82, in which case, individual ones of the electrode contacts 82 are selected one at a time for delivery of the electrical pulse trains in a monopolar mode.

Initially, in order to trigger a peripherally located fascicle or fascicles 15a innervating the tongue protrusor muscles, all of the electrode contact sets may be tested using regular, constant amplitude pulse trains having a defined pulse duration and frequency, as shown in FIG. 7. If no peripherally located fascicle 15a innervating the tongue protrusor muscles is triggered, all of the electrode contact sets may be tested using pre-conditioning pulse trains, such as that shown in FIG. 8, in order to trigger any centrally located fascicle or fascicles 15b that may possibly innervate the tongue protrusor muscles.

Once an optimal electrode contact set (or sets) is determined, the IPG 52 is programmed to the selected optimal electrode contact set (or sets) using the clinician programmer 56 (step 112). The IPG 52 can be turned on with the clinician programmer 56 or the patient programmer 58. Or, the patient can turn the IPG 52 to an ON setting, e.g., by tapping the area of the body over the implanted IPG 52 multiple times in quick succession or by using the patient programmer 64 (step 114). The IPG 52 may be turned ON when the patient wishes to sleep, or OFF, when the patient is awake during the day. In the ON position, the IPG 52 will provide, through the selected electrode contact or contacts, a stimulus train (or stimulus burst) at the programmed setting. Stimulation will move the tongue forward while the patient is asleep, so that during any obstructive apneic event, the patient will not be prevented from breathing. As such, when the IPG 52 is in the ON position, a train of pulse stimulation occurs at every breathing inspiration.

To save battery power, the IPG 52 may only provide therapy under a specific set of circumstances, e.g., if the patient is sleeping in an apneic position. To this end, the IPG 52 may determine if the patient is in an apneic position by measuring an orientation of the body of the patient (step 116), and if so, then determine if the patient is sleeping by measuring a physiological parameter indicative of whether the patient is sleeping (step 118).

If the patient is sleeping in an apneic position, the physiological artifacts caused by respiration are sensed and stored (step 120), the next projected onset of an inspiratory phase of the respiratory cycle is determined based on the sensed physiological artifacts (step 122), and electrical stimulation energy (e.g., an electrical pulse train) is delivered to the programmed electrode contact set in synchronization with a respiratory cycle based on the sensed physiological artifacts, and in particular, immediately before, at, or right after the next projected onset of the inspiratory phase of the respiratory cycle (step 124), thereby treating the OSA.

If the electrical pulse train is conventional in nature, one or more peripherally located nerve fascicles 15a in the HGN trunk 14 (presumably, the peripherally located nerve fascicle(s) 15a adjacent to the programmed electrode contact set) are triggered. If the electrical pulse train is a pre-conditioning pulse train, one or more peripherally located nerve fascicles 15a in the HGN trunk 14 will be pre-conditioned, and rendered not excitable, by the initial pre-conditioning current or voltage amplitude, while one or more centrally located nerve fascicles 15b in the HGN 14 will be triggered/activated by the subsequently delivered higher stimulating current or voltage amplitude.

Figure 10:
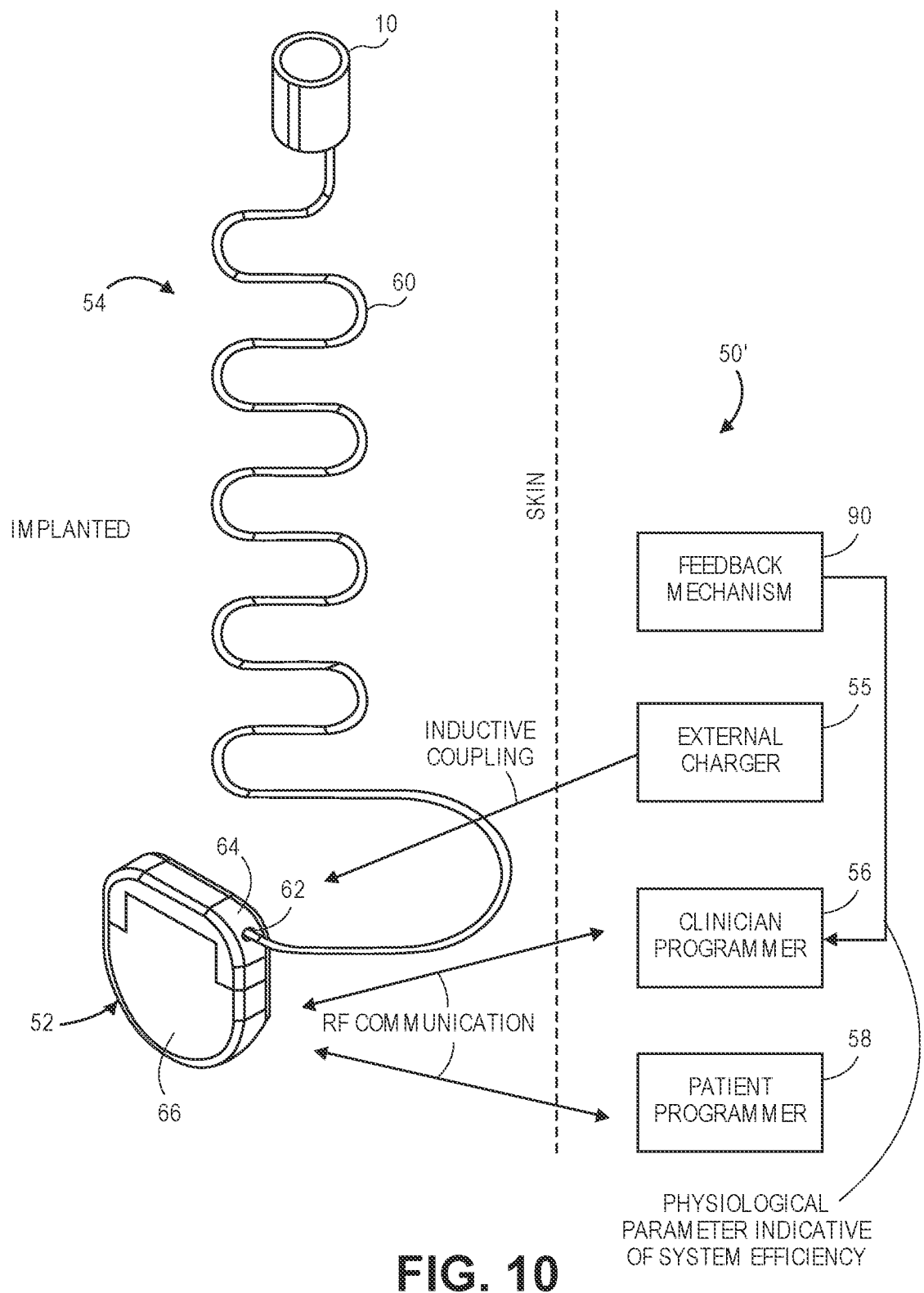
FIG. 10 is a plan view of a stimulation system constructed in accordance with another embodiment of the present inventions.

Referring now to FIG. 10, another embodiment of a stimulation system 50' that selectively stimulates the fascicles of the trunk 14 of the HGN 12 that innervate the tongue protrusor muscles for treating OSA will now be described. The stimulation system 50' is similar to the stimulation system 50' illustrated in FIG. 2, with the exception that the stimulation system 50' additionally comprises a feedback mechanism 90 that can titrate stimulation system 50' in a clinical setting in order to provide chronic therapy to a patient suffering from OSA.

The feedback mechanism 90 of the system 50 is capable of sensing a physiological parameter indicative of the efficacy in treating a patient's obstructive sleep apnea. In conjunction with the feedback mechanism 90, the clinician programmer 56 can be used to determine the best set or sets of electrode contacts 82, along with other stimulation parameters (e.g., stimulation pulse amplitude, stimulation pulse width, stimulation pulse frequency, and number of stimulus pulses in a pulse train, or burst and frequency of the stimulation pulses), that optimally recruits the target fascicles of the HGN trunk 14 that controls the protrusor muscle which moves the tongue forward.

The system 50' can be titrated the first time right after implantation of the nerve cuff electrode 10 or during clinical follow-up sessions. The system 50' can also be titrated during the implantation surgery itself, during a traditional sleep study, a drug induced sleep study, or other appropriate setting. The system 50' can be titrated while the patient is asleep, or it could be performed sometimes with the patient awake.

The clinician programmer 56 may be operated to iteratively test different sets of electrode contacts 82 of the nerve cuff electrode 10 to determine the set or sets electrode contacts 82, along with the corresponding types of electrical pulse trains, that provides the best therapy for treating the OSA of the patient. For the purposes of this patent disclosure, a set of electrode contacts 82 may include only one electrode contact 82 or may include multiple electrode contacts 82.

Figure 7A:
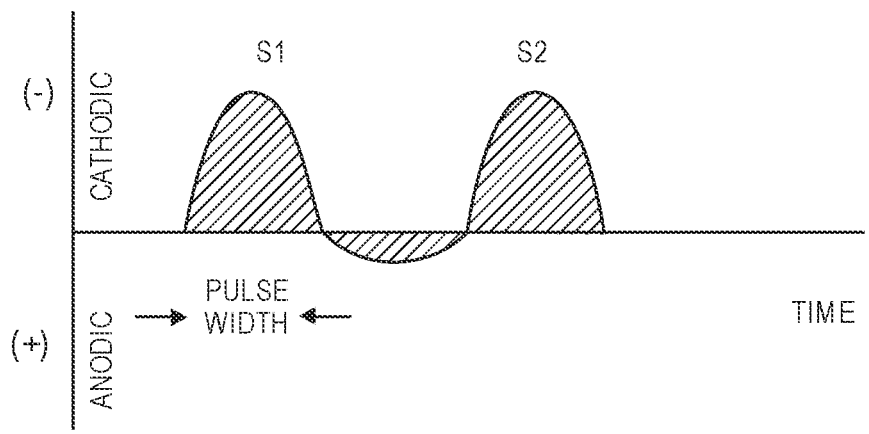
FIG. 7a is a diagram of an electrical pulse train that can be generated by the stimulation system of FIG. 2.
Figure 7B:
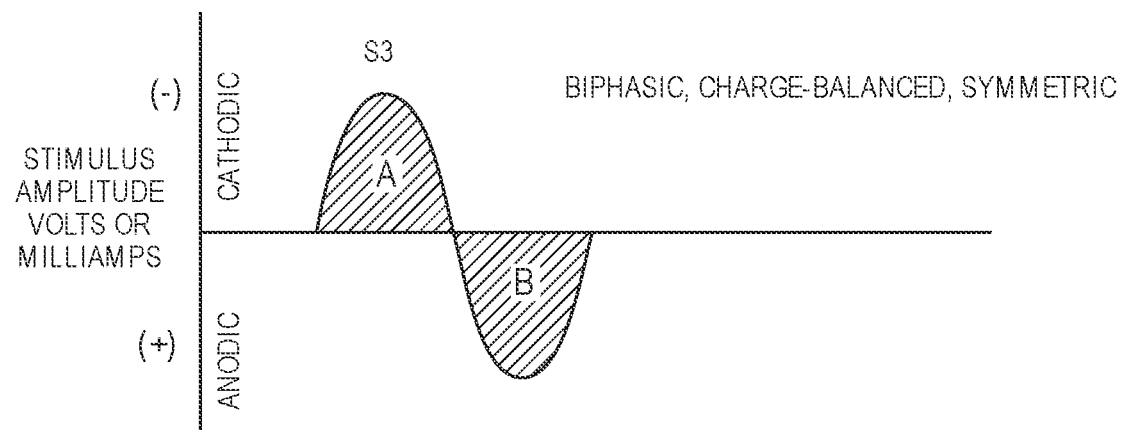
FIG. 7b is a diagram of a bi-phasic, charge-balanced, symmetrical electrical pulse train that can be generated by the stimulation system of FIG. 2.
Figure 7C:
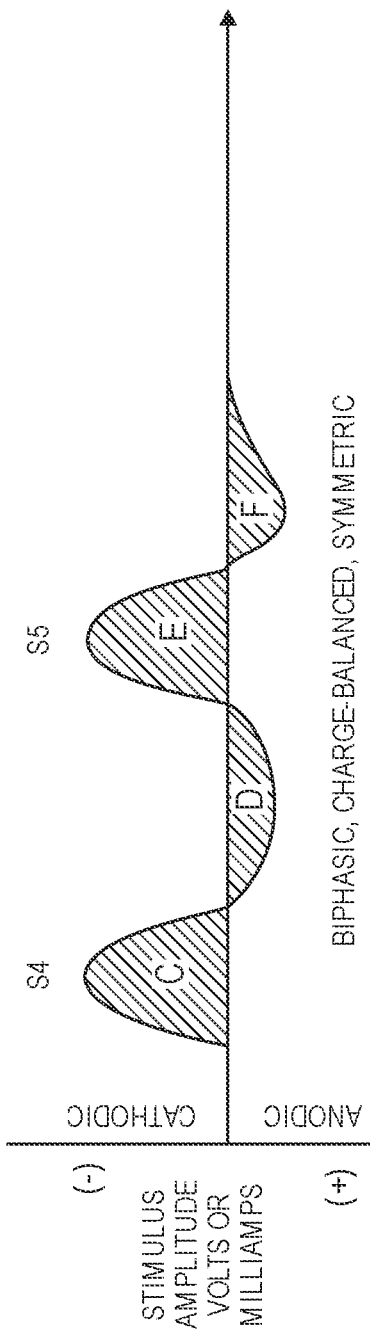
FIG. 7c is a diagram of a bi-phasic, charge-balanced, asymmetrical electrical pulse train that can be generated by the stimulation system of FIG. 2.
Figure 7D:
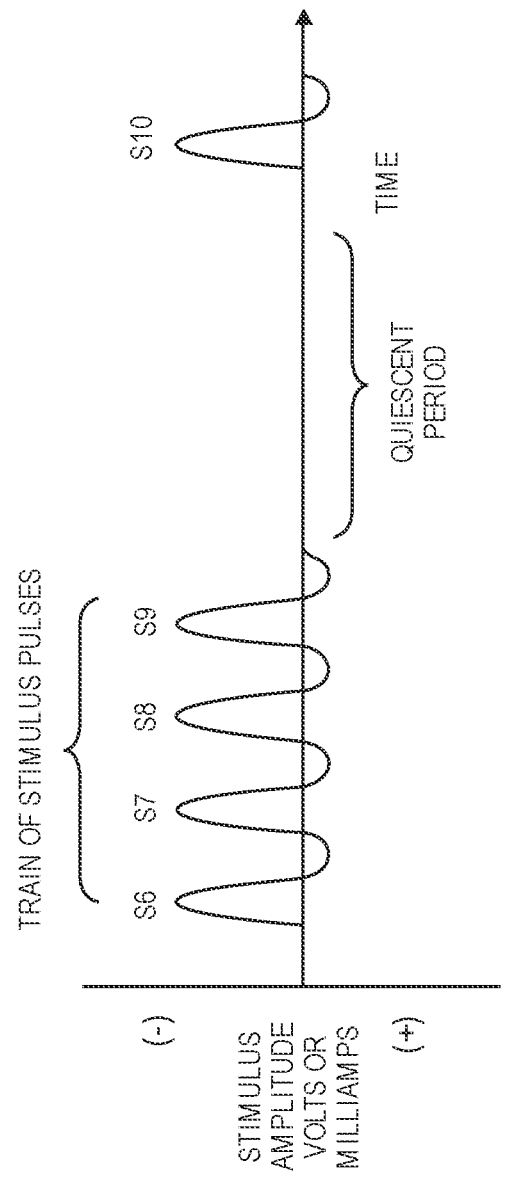
FIG. 7d is a diagram of a bi-phasic, asymmetrical electrical pulse train having a quiescent period that can be generated by the stimulation system of FIG. 2.

As an example, using an asymmetrical (peak cathodic amplitude larger than peak anodic amplitude), biphasic, charge-balanced, stimulus such as shown in FIG. 7(c) and referring to FIG. 5 or FIG. 6, the electrode contact 82 selected could be a monopolar set, with the outer case 66 of the IPG 52 turned on as indifferent, return electrode contact. Then each electrode contact, 82a, 82b, 82c, 82d, 82e, and 82f can be tested for successively for its efficacy.

Sometimes a monopolar stimulation can have two stimulating (functioning cathodic) electrode contacts 82, e.g., the outer case 66 of the IPG 52 functions as the indifferent electrode (anode), electrode contact 82a and electrode contact 82b concurrently function as stimulating cathodes. In this latter arrangement, using two stimulating cathodes concurrently, true current steering can be accomplished. For example, if electrode contact 82a outputs 50% of the total current while, at the same time, electrode contact 82b outputs 50% of the total current, the net effect is to create a virtual electrode that appears to be an electrode contact that is positioned right in between the two electrode contacts, 82a and 82b. In other cases, the current output may be uneven, for example 70% of total current output for contact 82a and 30% of total current output from contact 82b. In that case the virtual electrode will be in between but closer to contact 82a than 82b. Current steering means that the center of electrical current density is somewhere between the centers of two adjacent electrodes and is an extremely powerful tool to "steer" the stimulation precisely between two electrode contacts.

In addition, the titration or fitting may test various sets of electrode contacts in bipolar stimulation mode. Examples of bipolar modes include: (A) 82a (stimulating cathode) and 82b (functioning anode); (B) 82a (stimulating cathode) and 82c (functioning anode); and (C) three electrode contacts in a tripolar arrangement, but still bipolar stimulation—82b (cathode), 82a (return anode) and 82c (return anode). Note there are opportunities for field shaping because 82a and 82c may both return 50% of the total current output from contact 82b. Alternatively, contacts 82a and 82c could sink different values of the total current, e.g. 40% and 60%. Of course, contact 82b has a throughput of 100% of the stimulating current at any instant in time. As the numbers of electrode contact increase, e.g. six electrode contacts, there are many combinations of electrode contacts that can be used, hence the need for a fitting or titrating step to choose an optimal set of electrode contacts, bipolar or monopolar stimulation, and stimulus amplitudes of individual contacts.

The clinician programmer 56 may automatically or manually cycle through each possible set of electrode contacts 82, score the set of electrode contacts 82, along with the electrical pulse train types, based on the output of the feedback mechanism 90, and select the best set or sets of electrode contacts 82 and electrical pulse trains based on the corresponding efficacy scores.

The efficacy of the selected set of electrode contacts 82, along with the corresponding electrical pulse train types, can be quantified using a scoring system, e.g., by assigning a score from 1 to 100 to the selected set of electrode contacts 82 and corresponding stimulation parameters, with 1 being the least effective, and 100 being the most effective. The clinician programmer 56 may apply a preset series of stimulation patterns for each of the sets of electrode contacts 82, while utilizing the feedback mechanism 90 to score the effectiveness of the settings. The clinical programmer 56 may use algorithms that recursively apply test stimulation patterns based upon earlier computed scores to converge on the optimal settings for a given patient.

If monopolar stimulation is assumed, different electrode contacts 82 may be selected in combination with the outer case 66, which serves as the return electrode contact. For example, if the nerve cuff electrode 10 has four electrode contacts labeled, #1, #2, #3, and #4, along with the outer case 66 as the first electrode contact, electrode contact #1 can be selected and tested, then electrode contact #2 can be selected and tested, then electrode contact #3 can be selected and tested, and then electrode contact #4 can be selected and tested. Of course, various combinations of electrode contacts can be tested. For example, along with the outer IPG case 66 as the indifferent or return electrode contact, electrode contact combination #1, #2 can be selected and tested, electrode contact combination #2, #3 can be selected and tested, electrode contact combination #3, #4 can be selected and tested, and electrode contact combination #3, #4 can be selected and tested. If bipolar stimulation is assumed, pairs of electrode contacts 82 may be selected. For example, twelve total bipolar, two electrode contact combinations can be selected—noting pair #1, and #4 can be different than #4 and #1, depending on which electrode contact 82 is functioning mainly as the active, stimulating contact.

Figure 11:
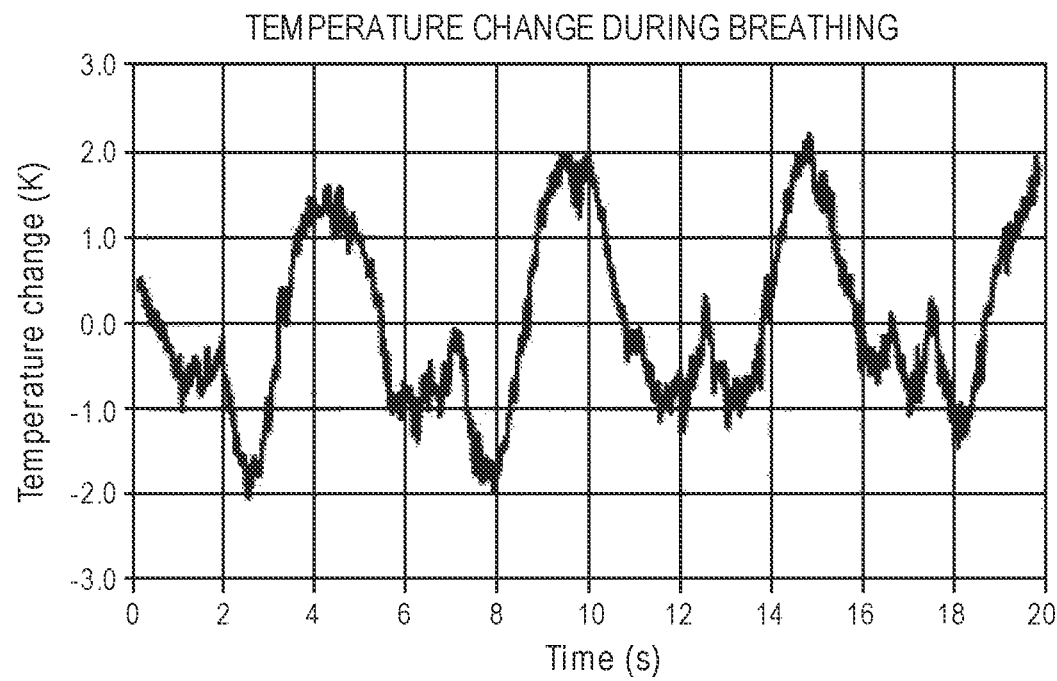
FIG. 11 is a diagram of an exemplary temperature change measurement taken by a feedback mechanism of the stimulation system of FIG. 10 from a breath during respiration of a patient.

The feedback mechanism 90 can take the form of any mechanism that can output a signal indicative of the efficacy of the treatment of OSA. Generally, during titration, the patient is either asleep or under general anesthesia. In one embodiment, the feedback mechanism 90 comprises a temperature sensor that can be located under the nose and/or close to the mouth of the patient to measure the temperature of the inhaled and exhaled air of the patient. Since inhaled air has a lower temperature than that of the exhaled air, the temperature of the inhaled and exhaled air is a good indicator of the respiratory cycle. The temperature change between the inhaled air and the exhaled air is best illustrated in FIG. 11, which shows an approximate ±2° K peak-to-peak difference in temperature between air inhaled through the nose and air exhaled from the nose. Thus, based on the signal output by the temperature sensor, the clinician programmer 56 can determine the beginning and ending of each inspiration phase in the respiratory cycle, as well as the efficiency of the inspiration phase (i.e., whether the patient is taking a full breath during the inspiration phase).

Based on this, the clinician programmer 56 can compute a score of the therapy provided by the current set up of the system 50, and in particular, the currently selected set of electrode contacts and corresponding stimulation parameters. For example, if the valleys of the signal output by the temperature sensor indicate a regular and normal pattern of inspiration during the respiratory cycle, the therapy score assigned to the current set up may be relatively high, whereas if the valleys of the signal output by the temperature sensor indicate a non-regular or abnormal pattern of inspiration during the respiratory cycle, the therapy score assigned to the current set up may be relatively low. Thus, the more efficient the inspiration phase of the respiratory cycle, the higher the therapy score, and the less efficient the inspiration phase of the respiratory cycle, the lower the therapy score.

Figure 12:
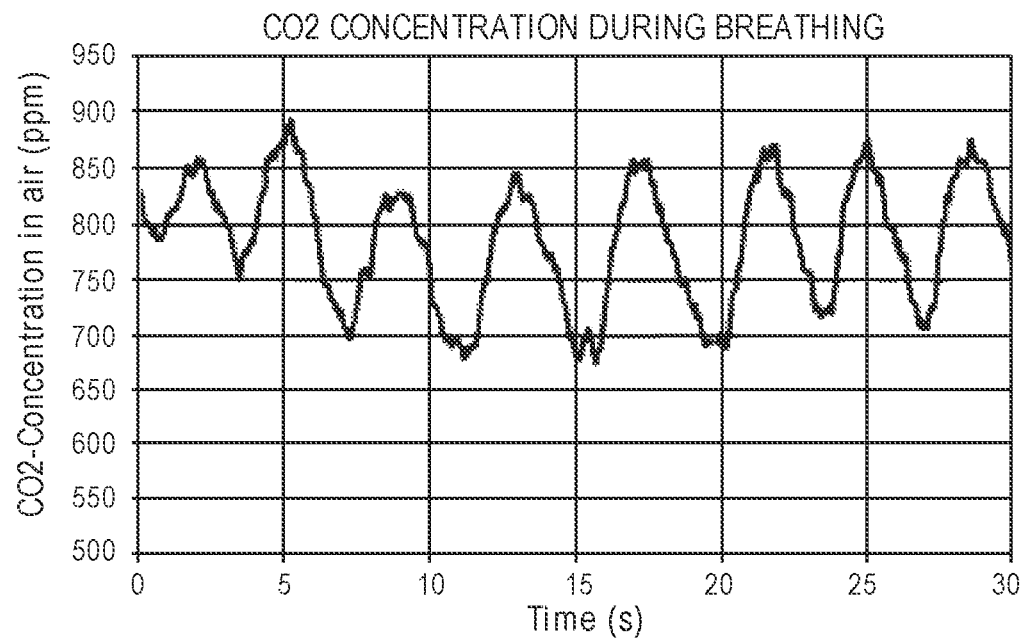
FIG. 12 is a diagram of an exemplary CO2 concentration measurement taken by a feedback mechanism of the stimulation system of FIG. 10 from a breath during respiration of a patient.

In another embodiment, the feedback mechanism 90 comprises a carbon dioxide (CO2) sensor that can be located under the nose and/or close to the mouth of the patient to measure the concentration of CO2 in the inhaled and exhaled air of the patient. Since inhaled air has a lower CO2 concentration than that of the exhaled air, the CO2 concentration of the inhaled and exhaled air is a good indicator of the respiratory cycle. The CO2 concentration change between the inhaled air and the exhaled air is best illustrated in FIG. 12, which shows an approximate ±85 ppm peak-to-peak difference in CO2 concentration between air inhaled through the nose and air exhaled from the nose. Thus, based on the signal output by the CO2 sensor, the clinician programmer 56 can determine the beginning and ending of each inspiration phase in the respiratory cycle, as well as the efficiency of the inspiration phase (i.e., whether the patient is taking a full breath during the inspiration phase).

In a similar manner described above with respect to the temperature sensor, the clinician programmer 56 can compute a score of the therapy provided by the current set up of the system 50, and in particular, the currently selected set of electrode contacts and corresponding stimulation parameters. That is, if the valleys of the signal output by the CO2 sensor indicate a regular and normal pattern of inspiration during the respiratory cycle, the therapy score assigned to the current set up may be relatively high, whereas if the valleys of the signal output by the CO2 sensor indicate a non-regular or abnormal pattern of inspiration during the respiratory cycle, the therapy score assigned to the current set up may be relatively low. Thus, the more efficient the inspiration phase of the respiratory cycle, the higher the therapy score, while the less efficient the inspiration phase of the respiratory cycle, the lower the therapy score.

In still another embodiment, the feedback mechanism 90 comprises one or more electro-myographic (EMG) sensors that measure the electrical potential generated by the muscle cells of the tongue in response to electrical stimulation of the HGN 12. The EMG sensor(s) may be incorporated into an oral appliance or mouth guard (not shown), such that the EMG sensor(s) is in surface contact with the appropriate muscle(s) of the tongue when the oral appliance or mouth guard is worn by the patient, or the EMG sensor(s) can take the form of needle electrodes that can be placed into the appropriate muscle(s) of the tongue. Alternatively, non-invasive EMG sensor(s) may be placed on the neck region of the patient to detect movement of the tongue caused by the electrical stimulation of the HGN.

Based on the EMG signals output by the EMG sensor(s), the clinician programmer 56 can compute a score of the therapy provided by the current set up of the system 50, and in particular, the currently selected set of electrode contacts and corresponding stimulation parameters. That is, the EMG activity sensed by the EMG sensor(s) in synchronization with the stimulation of the HGN 12 is indicative of activation of the tongue protrusor muscles. If the magnitude of the EMG activity is relatively high, indicating a strong activation of the tongue protrusor muscles, the therapy score assigned to the current set up may be relatively high, whereas if the magnitude of the EMG activity is relatively low, indicating no or weak activation of the tongue protrusor muscles, the therapy score assigned to the current set up may be relatively low.

In still another embodiment, the feedback mechanism 90 comprises a camera that captures pictures of the airway of the patient, thereby providing an indication of how well the obstruction in the airway of the patient is eliminated in response to electrical stimulation of the HGN 12. The camera may be on the end of an endoscope typically inserted through the nasal cavity. The clinician programmer 56 may have image analysis software that computes the area of the airway opening shown in the picture provided by the camera, and based on this computed area, computes a score of the therapy provided by the current set up of the system 50, and in particular, the currently selected set of electrode contacts and corresponding stimulation parameters. Thus, if the computed area of the airway opening is relatively large, the therapy score assigned to the current set up may be relatively high, whereas if the computed area of the airway opening is relatively low, the therapy score assigned to the current set up may be relatively low.

In yet another embodiment, the feedback mechanism 90 comprises an inertial sensor (e.g., an accelerometer or gyroscope) that measures the movement of the tongue in response to electrical stimulation of the HGN 12. The inertial sensor may be incorporated into an oral appliance or mouth guard (not shown). Based on the signals output by the inertial sensor, the clinician programmer 56 can compute a score of the therapy provided by the current set up of the system 50, and in particular, the currently selected set of electrode contacts and corresponding stimulation parameters. That is, the motion activity sensed by the inertial sensor in synchronization with the stimulation of the HGN 12 is indicative of movement of the tongue. If the magnitude of the signals is relatively high, indicating a strong activation of the tongue protrusor muscles, the therapy score assigned to the current set up may be relatively high, whereas if the magnitude of the signals is relatively low, indicating no or weak activation of the tongue protrusor muscles, the therapy score assigned to the current set up may be relatively low.

Figure 13:
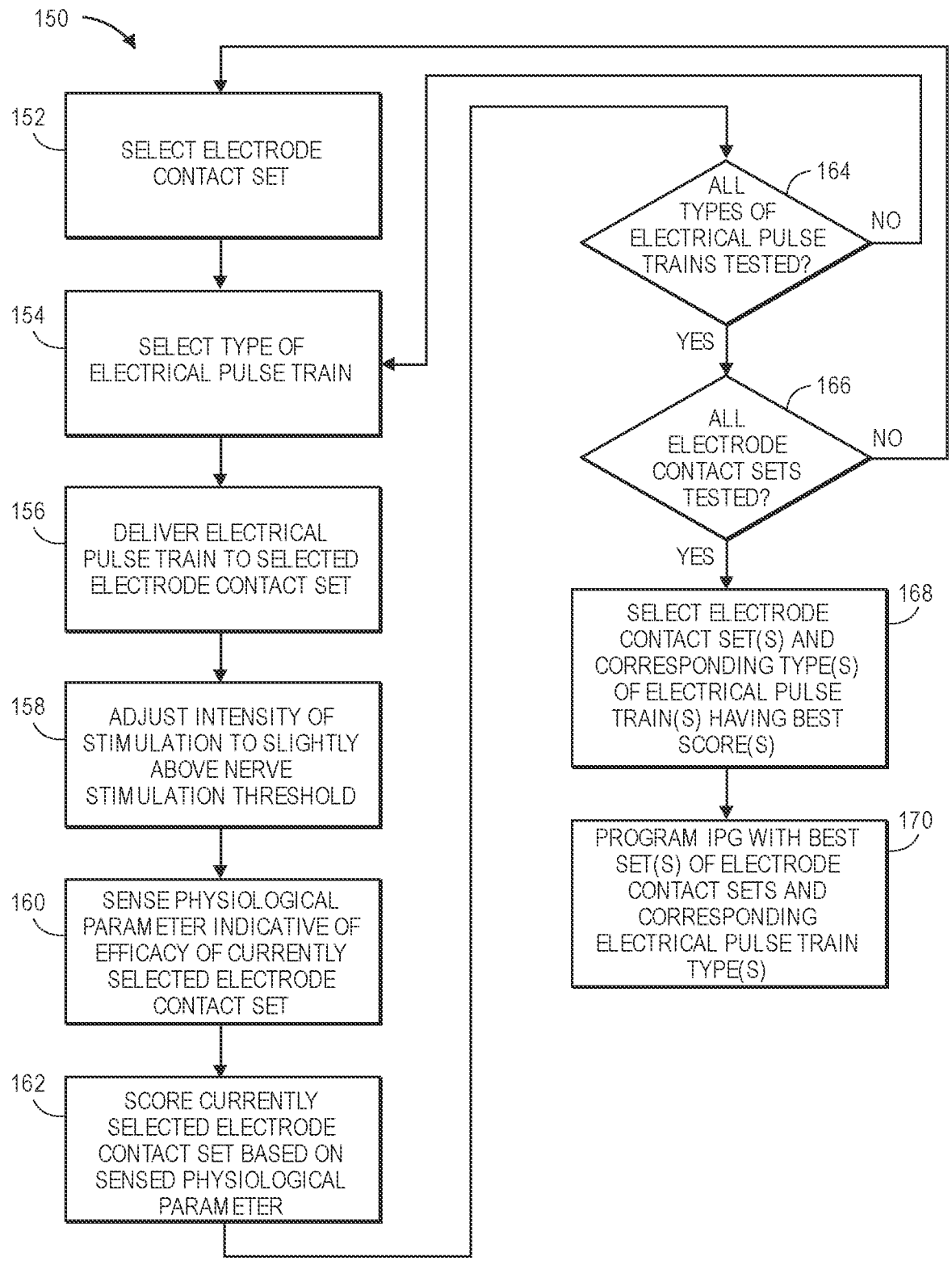
FIG. 13 is a flow diagram illustrating one method of titrating or fitting the stimulation system of FIG. 10 to a patient.

Referring now to FIG. 13, one embodiment of the method 150 of fitting or titrating the system 10 to a particular patient in a clinical setting in order to subsequently provide chronic therapy will be described. By "fitting" or "titrating" is meant herein the identification and selection of an optimal set of electrode contacts, selection of monopolar or bipolar stimulation, the determination of stimulus parameters, e.g., amplitude, frequency, pulsewidth, and whether to apply preconditioning pulses. Advantageously, once the nerve cuff electrode 10 is implanted within the patient, and in an embodiment of the method, around the trunk portion 14 of the HGN 12 of the patient, embodiments of the fitting procedure will aid in identifying the preferred electrode contact or contacts of the nerve cuff electrode 10 to use in order to optimally recruit the fascicles of the HGN trunk 14 that innervate the muscles that control protraction of the tongue. In this fitting procedure, it is important also to avoid stimulating muscles that control tongue retraction. The fitting procedure may also be used to set the stimulus parameters, e.g., stimulus pulse width, stimulus frequency, number of stimulus pulses in a pulse train, or burst and frequency of the stimulus pulses, and if a pre-conditioning stimulus pulse train is used, the fitting procedure may be used to determine the intensity of the stimulation pulses relative to the pre-conditioning pulses in terms of pulse amplitudes or pulse widths. The fitting procedure can also be used to initially determine whether a pre-conditioning pulse train is needed at all, or whether a simple electrical pulse train without pre-conditioning will suffice to activate the desired fascicles in the HGN 12.

First, a set of electrode contacts 82 of the nerve cuff electrode 10 is selected (step 152), and the type of the electrical pulse train (e.g., amplitude, pulse width, pulse duration, monopolar or bipolar mode, conventional or pre-conditioning, etc.)) generated by the system 50' will be selected (step 154). The electrical pulse train may be, e.g., a regular, constant amplitude pulse train having a defined train duration and frequency, such as that shown in FIG. 7, or a pre-conditioning electrical pulse train, such as that shown in FIG. 8, and may be either bipolar or monopolar stimulation.

Then, the electrical pulse train is delivered to the selected electrode contact(s), for example, 82 (*a*)-(*f*), in accordance with the selected electrical pulse parameters (step 156), and the intensity of the stimulation is adjusted (by adjusting pulse amplitude and/or pulse width) from below nerve stimulation threshold to slightly above nerve stimulation threshold (step 158). Next, the efficacy of the selected set electrode contacts 82 in treating the OSA of the patient is determined.

In particular, the feedback mechanism 90 senses a physiological parameter indicative of the efficacy of the currently selected set of electrode contacts 82 and corresponding set of stimulation parameters in treating the OSA of the patient (step 160). The clinician programmer 56 then scores the set of electrode contacts 82, along with the set of stimulation parameters, based on the output of the feedback mechanism 90 (step 162). If all possible selections of electrical pulse trains for currently selected set of electrode contacts 82 have not yet been tested (step 164), the clinician programmer 56 returns to step 154, where a different set of stimulation parameters is selected for the currently selected electrode contact set, and steps 156-164 are repeated. If all types of electrical pulse trains for the currently selected set of electrode contacts 82 has been tested (step 164), and if not all possible electrode sets of electrode contacts 82 have been tested (step 166), the fitting procedure returns to step 152, where a different set of electrode contacts 82 is selected and tested by repeating steps 154-166. If all possible electrode sets of electrode contacts 82 have been tested (step 166), the clinician, using the clinician programmer 56 selects the best set or sets of electrode contacts 82 and corresponding type of electrical pulse train, preferably, those with the best therapy score(s) (step 168), and programs the IPG 52 with the best set or sets of electrode contacts 82 and corresponding types of electrical pulse trains (step 170).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of stimulating a nerve bundle of a patient to treat an ailment, comprising:
   disposing at least one electrode contact adjacent the nerve bundle; and
   delivering an electrical pulse train to at least one of the electrode contacts, thereby treating the ailment,
   wherein the nerve bundle has one or more peripherally located nerve fascicles and one or more centrally located nerve fascicles radially deeper within the nerve bundle than the peripherally located nerve fascicles,
   wherein the electrical pulse train has an initial, preconditioning current or voltage amplitude and a subsequent higher stimulating current or voltage amplitude, such that the one or more peripherally located nerve fascicles are preconditioned by the initial preconditioning current or voltage amplitude, and
   the one or more centrally located nerve fascicles are triggered by the higher stimulating current or voltage amplitude, while the one or more preconditioned peripherally located nerve fascicles are not triggered by the higher stimulating current or voltage amplitude.

2. The method of claim 1, wherein the nerve has a diameter in the range of 2.5 mm to 4.0 mm.

3. The method of claim 1, wherein the at least one electrode contact comprises a plurality of electrode contacts circumferentially disposed around the nerve.

4. The method of claim 3, wherein the electrode contacts are axially aligned with each other.

5. The method of claim 3, wherein the plurality of electrode contacts comprises at least three electrode contacts.

6. The method of claim 3, wherein the plurality of electrode contracts comprises at least six electrode contacts.

7. The method of claim 3, wherein the plurality of electrode contacts circumferentially span at least a 180-degree arc around the nerve.

8. The method of claim 3, wherein the plurality of electrode contacts circumferentially span at least a 270-degree arc around the nerve.

9. The method of claim 3, wherein a center-to-center spacing of each pair of adjacent ones of electrode contacts is equal to or less than twice the width of each electrode contact of the respective pair of electrode contacts.

10. The method of claim 1, wherein the at least one electrode contact comprises a pair of adjacent ones of the electrode contacts, and the electrical pulse train is delivered between the pair of adjacent ones of the electrode contacts in a bipolar mode.

11. The method of claim 1, further comprising
    sensing physiological artifacts that are caused by respiration, and
    delivering the electrical pulse train to the at least one electrode contact in synchronization with a respiratory cycle based on the sensed physiological artifacts.

12. The method of claim 11, further comprising
    determining the next projected onset of an inspiratory phase of the respiratory cycle based on the sensed physiological artifacts, and
    delivering the electrical pulse train to the at least one electrode contact immediately before, at, or right after the next projected onset of the inspiratory phase of the respiratory cycle.

13. The method of claim 11, further comprising storing data representative of the sensed physiological artifacts.

14. The method of claim 11, wherein the physiological artifacts are sensed by at least one of an accelerometer, a gyroscope, a pressure sensor, a bioimpedance sensor, an ECG electrode, and a temperature sensor.

15. The method of claim 1, further comprising:
    measuring a physiological parameter of the patient; and
    determining an efficacy of the delivered electrical pulse train in treating the ailment of a patient based on the measured physiological parameter.

16. The method of claim 15, wherein measuring the physiological parameter comprises one or more of:
    measuring the temperature of inhaled and/or exhaled air of a patient,
    measuring a concentration of $CO_2$ in inhaled and/or exhaled air of the patient,
    measuring the electrical potential generated by the muscle cells of a tongue of the patient,
    capturing pictures of the airway of the patient, and
    measuring the movement of the tongue of the patient.

17. The method of claim 15, wherein the nerve is a trunk of a hypoglossal nerve (HGN), and wherein the measured physiological parameter is a measured movement of the tongue in response the electrical pulse train delivered to the HGN in treating the ailment of a patient.

18. The method of claim 17, wherein the movement of the tongue is measured by an inertial sensor incorporated into an oral appliance.

19. The method of claim 15, wherein the nerve is a trunk of a hypoglossal nerve (HGN), and wherein the measured physiological parameter is a measured electrical potential generated by the muscle cells of the tongue in response to the electrical pulse train delivered to the HGN in treating the ailment of a patient.

20. The method of claim 19, wherein the electrical potential generated by the muscle cells of the tongue is measured by an electromyographic (EMG) sensor placed on or in the neck of the patient.

21. The method of claim 1, wherein the nerve is a trunk of a hypoglossal nerve (HGN).

22. The method of claim 21, wherein the at least one electrode contact is located on the HGN trunk proximal to a medial branch of the HGN trunk.

23. The method of claim 21, wherein the ailment is obstructive sleep apnea (OSA), and stimulation of the centrally located nerve fascicles treats the OSA.

24. The method of claim 1, wherein the electrical pulse train is generated by a neurostimulator, the method further comprising toggling the neurostimulator between an OFF state and an ON state in response to at least one tap on the neurostimulator by the patient.

25. The method of claim 24, further comprising sensing the at least one tap on the neurostimulator by the patient using an inertial sensor.

26. The method of claim 25, wherein the inertial sensor comprises at least one of an accelerometer and a gyroscope.

27. The method of claim 1, wherein the electrical pulse train is generated by a neurostimulator, the method further comprising toggling the neurostimulator between an OFF state and an ON state in response to sensing a magnetic field from an external magnet.

* * * * *